United States Patent
Ahn et al.

(10) Patent No.: US 9,759,665 B2
(45) Date of Patent: Sep. 12, 2017

(54) PANEL INSPECTING APPARATUS AND METHOD

(71) Applicants: Myoung-ki Ahn, Yongin-si (KR); Jin-woo Ahn, Suwon-si (KR); Tae-yong Jo, Seoul (KR); Hyeong-min Ahn, Yongin-si (KR); Tae-hyoung Lee, Suwon-si (KR)

(72) Inventors: Myoung-ki Ahn, Yongin-si (KR); Jin-woo Ahn, Suwon-si (KR); Tae-yong Jo, Seoul (KR); Hyeong-min Ahn, Yongin-si (KR); Tae-hyoung Lee, Suwon-si (KR)

(73) Assignee: Samsung Electronics Co., Ltd., Gyeonggi-Do (KR)

( * ) Notice: Subject to any disclaimer, the term of this patent is extended or adjusted under 35 U.S.C. 154(b) by 10 days.

(21) Appl. No.: 14/712,205

(22) Filed: May 14, 2015

(65) Prior Publication Data
US 2016/0097726 A1   Apr. 7, 2016

(30) Foreign Application Priority Data
Oct. 2, 2014   (KR) .................. 10-2014-0133553

(51) Int. Cl.
*G01N 21/00*   (2006.01)
*G01N 21/88*   (2006.01)
*G01N 21/95*   (2006.01)

(52) U.S. Cl.
CPC ......... *G01N 21/8806* (2013.01); *G01N 21/95* (2013.01); *G01N 2021/9513* (2013.01)

(58) Field of Classification Search
CPC ... G06T 7/0085; G06T 7/0002; G06T 7/0079; G01N 21/8806; G01N 21/8851; G01N 21/958; G01N 21/9503; G01N 2021/9513
USPC ......... 356/237.1–237.5, 239.1, 239.2, 239.7, 356/239.8, 614–623; 250/559.36
See application file for complete search history.

(56) References Cited

U.S. PATENT DOCUMENTS

| | | | |
|---|---|---|---|
| 7,366,344 B2 * | 4/2008 | Sim .................... | G06T 7/001 382/149 |
| 7,478,569 B2 | 1/2009 | Bossi et al. | |
| 7,486,101 B2 | 2/2009 | Lin et al. | |
| 7,683,606 B2 | 3/2010 | Kang et al. | |
| 7,982,479 B2 | 7/2011 | Wang et al. | |
| 8,023,111 B2 * | 9/2011 | Hayashi .......... | G01N 21/9503 356/237.5 |
| 8,072,437 B2 | 12/2011 | Miller et al. | |

(Continued)

FOREIGN PATENT DOCUMENTS

| | | |
|---|---|---|
| DE | 102004010376 A1 * | 9/2005 |
| JP | 2007-147433 * | 6/2007 |
| KR | 10-1075588 | 10/2011 |

*Primary Examiner* — Hoa Pham
(74) *Attorney, Agent, or Firm* — Harness, Dickey & Pierce, P.L.C.

(57) ABSTRACT

A panel inspecting apparatus and method may accurately inspect image quality of a curved portion of a panel with relatively small inspecting cost and time, and the panel inspecting apparatus may have a relatively simple structure. The panel inspecting apparatus includes a support on which a panel is disposed, a mirror corresponding to a curved area of the panel, a lens configured to receive an image from the panel and an image reflected by the mirror and focus the images, and an image sensor configured to capture the images transferred via the lens.

15 Claims, 21 Drawing Sheets

(56) References Cited

U.S. PATENT DOCUMENTS

| | | | |
|---|---|---|---|
| 8,089,622 B2 * | 1/2012 | Birkner | G01N 21/9503 356/237.5 |
| 8,576,555 B2 | 11/2013 | Misawa | |
| 2004/0169869 A1 * | 9/2004 | Shin | G01N 21/9501 356/635 |
| 2006/0238494 A1 | 10/2006 | Narayanaswami et al. | |
| 2007/0138679 A1 | 6/2007 | Lin et al. | |
| 2007/0222977 A1 * | 9/2007 | Hayashi | G01N 21/9501 356/237.2 |
| 2008/0212084 A1 * | 9/2008 | Watkins | G01N 21/9503 356/237.5 |
| 2008/0225281 A1 * | 9/2008 | Komuro | G01N 21/9503 356/237.2 |
| 2009/0066944 A1 * | 3/2009 | Gauffre | G01N 21/9054 356/240.1 |
| 2009/0097018 A1 * | 4/2009 | Watanabe | G01B 11/30 356/237.2 |
| 2009/0201495 A1 * | 8/2009 | Hiramoto | G01B 11/306 356/243.4 |
| 2010/0072490 A1 | 3/2010 | Kerr et al. | |
| 2011/0199480 A1 * | 8/2011 | Lev | G01N 21/9503 348/126 |
| 2012/0019482 A1 | 1/2012 | Wang | |
| 2013/0169790 A1 | 7/2013 | Xiao et al. | |
| 2015/0077742 A1 * | 3/2015 | Wootton | G01N 21/8806 356/239.3 |
| 2015/0198539 A1 * | 7/2015 | Seong | G01N 21/958 348/128 |

* cited by examiner (a)

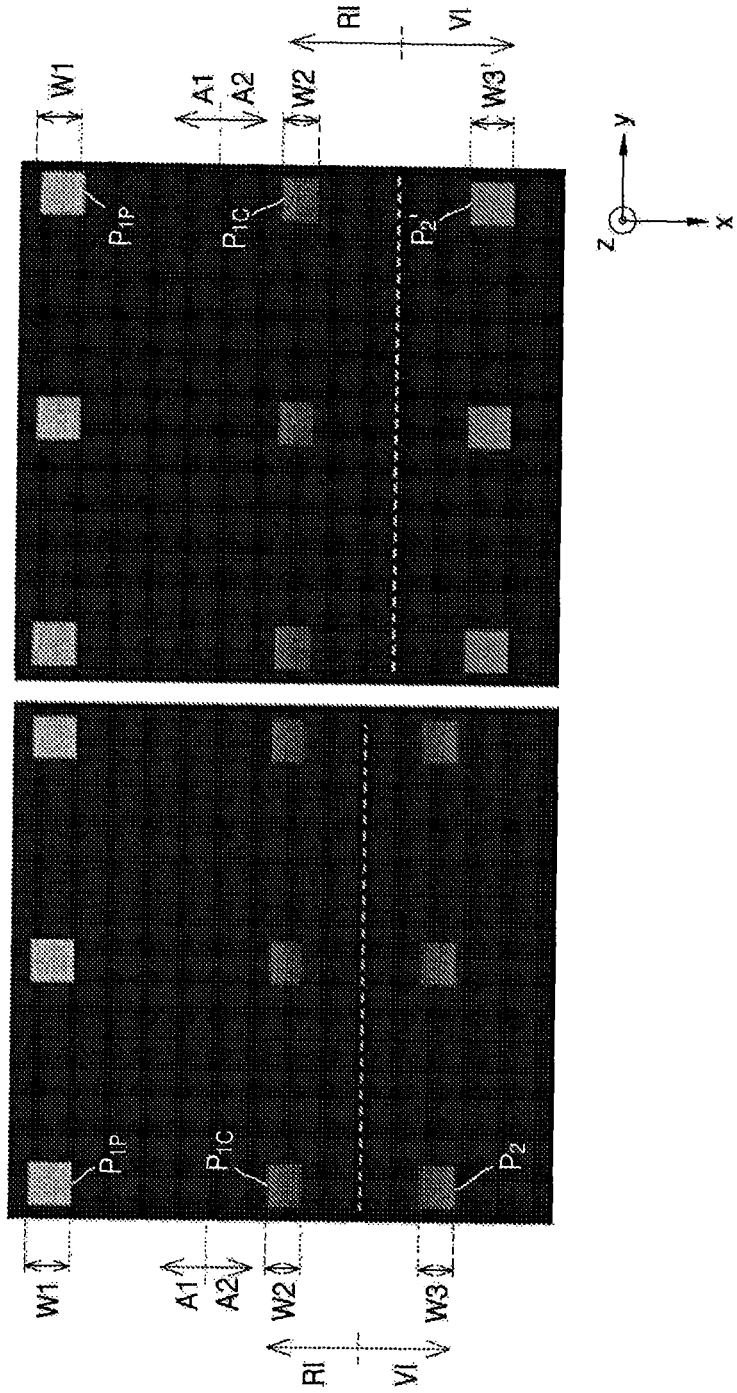

PANEL INSPECTING APPARATUS AND METHOD

CROSS-REFERENCE TO RELATED APPLICATION

This application claims priority under 35 U.S.C. §119 to Korean Patent Application No. 10-2014-0133553, filed on Oct. 2, 2014, in the Korean Intellectual Property Office, the disclosure of which is incorporated herein in its entirety by reference.

BACKGROUND

Some of the inventive concepts relate to inspecting a panel, and more particularly, to an apparatuses and/or methods of inspecting image quality of a panel including a curved surface.

In general, display panels, e.g., liquid crystal display (LCD) panels, light-emitting diode (LED) panels, and organic light-emitting diode (OLED) panels, may have faulty pixels due to defective patterns or particles (e.g., impurities) in the display panels. Accordingly, various inspecting equipment are used to inspect whether the display panels are defective. A visual inspecting apparatus (e.g., Auto Visual Tester (AVT)) captures an image of a display panel by using a camera, inspects image quality by analyzing the captured image, and automatically classifies the inspected display panel. For example, the visual inspecting apparatus may analyze an image captured when a display panel is operating and determine that an area different from surrounding colors or patterns is a defective area. The defective area may be formed due to, for example, particles in the display panel or due to a defective circuit.

SUMMARY

The inventive concepts provide panel inspecting apparatuses and/or methods that are capable of accurately inspecting image quality of a curved portion of a panel, simplifying a structure of the apparatus, and/or reducing inspecting cost and time.

According to an aspect of the inventive concepts, a panel inspecting apparatus includes a support on which a panel is disposed, at least one mirror corresponding to at least one curved area of the panel, at least one lens configured to receive an image from the panel and an image reflected by the at least one mirror, and an image sensor configured to capture the images transferred via the at least one lens.

According to another aspect of the inventive concepts, a panel inspecting apparatus includes at least one flat mirror that corresponding to at least one curved area of a panel, and the at least one flat mirror is configured to reflect at least one image of the at least one curved area at an edge of a panel, a lens configured to receive an image from the panel and the at least one image reflected by the at least one flat mirror, and an image sensor configured to capture the images transferred via the lens.

According to still another aspect of the inventive concepts, a panel inspecting apparatus includes at least one curved mirror corresponding to at least one curved area of a panel, the curved mirror configured to reflect an image of the curved area, a lens configured to receive an image from the panel and the image reflected by the at least one curved mirror, and an image sensor configured to capture the images transferred via the lens.

According to yet another aspect of the inventive concepts, a panel inspecting method includes disposing at least one mirror near at least one curved area of a panel, and inspecting the at least one curved area of the panel using the at least one mirror.

According to even another aspect of the inventive concepts, a panel inspecting apparatus includes a support configured to receive a panel thereon, the panel including a flat area and a curved area, at least one mirror configured to reflect an image of the curved area of the panel, at least one lens configured to receive image information of the flat area and image information of the curved area reflected from the at least one mirror, and an image sensor configured to convert the image information of the flat area and the image information of the curved area received via the lens to electric signals.

BRIEF DESCRIPTION OF THE DRAWINGS

Example embodiments of the inventive concepts will be more clearly understood from the following detailed description taken in conjunction with the accompanying drawings in which:

FIGS. 5A and 5B are photographs obtained by inspecting an image of a pattern in a curved area of a panel when a mirror is disposed perpendicularly and at an obtuse angle in a panel inspecting apparatus according to an example embodiment, respectively;

DETAILED DESCRIPTION

Figure 1A:
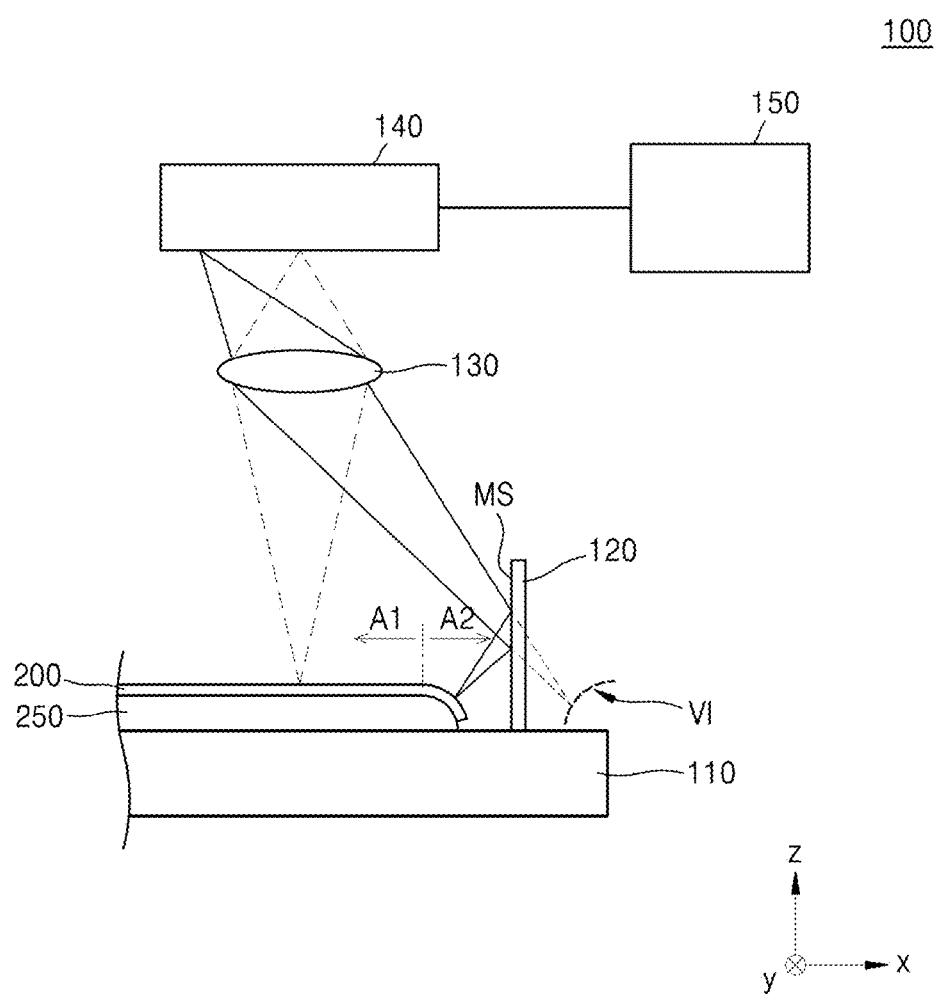
FIG. 1A is a conceptual view of a panel inspecting apparatus according to an example embodiment.

Reference will now be made in detail to example embodiments, some examples of which are illustrated in the accompanying drawings. The example embodiments of the present inventive concepts are provided to fully describe the present inventive concepts to one of ordinary skill in the art to which the present inventive concepts pertains. The example embodiments may have different forms and should not be construed as being limited to the descriptions set forth herein. Instead, the example embodiments are merely provided to more fully convey the spirit and scope of the present inventive concepts to one of ordinary skill in the art. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "connected to" another element, the element may be directly connected to the other element, or intervening elements may be present. Similarly, it will be understood that when an element is referred to as being "provided on" another element, the element may be directly formed on the other embodiment, or intervening elements may be present. In addition, structures or sizes of components in the drawings may be exaggerated for convenience of description and clarity, and features and elements that are not related to the description have not been included. Like reference numerals in the drawings denote like elements. The terms used in the present specification are merely used to describe particular example embodiments, and are not intended to limit the inventive concepts.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of example embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The terminology used herein is for the purpose of describing particular example embodiments only and is not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized example embodiments (and intermediate structures). As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing.

Although corresponding plan views and/or perspective views of some cross-sectional view(s) may not be shown, the cross-sectional view(s) of device structures illustrated herein provide support for a plurality of device structures that extend along two different directions as would be illustrated in a plan view, and/or in three different directions as would be illustrated in a perspective view. The two different directions may or may not be orthogonal to each other. The three different directions may include a third direction that may be orthogonal to the two different directions. The plurality of device structures may be integrated in a same electronic device.

Hereinafter, some example embodiments will be explained in further detail with reference to the accompanying drawings.

Figure 1B:
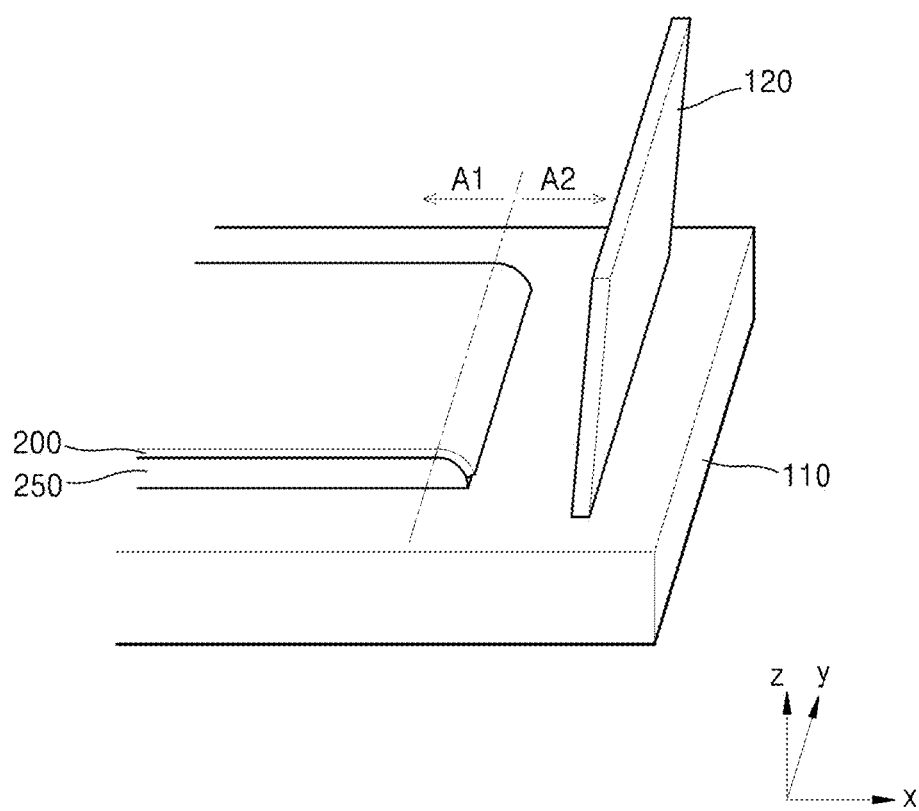
FIG. 1B is a detailed perspective view of a support, a mirror, and a panel of the panel inspecting apparatus of FIG. 1A.

FIG. 1A is a conceptual view of a panel inspecting apparatus 100 according to an example embodiment. FIG. 1B is a detailed perspective view of a support 110, a mirror 120, and a panel 200 of the panel inspecting apparatus 100 of FIG. 1A.

Referring to FIGS. 1A and 1B, the panel inspecting apparatus 100 according to the present example embodiment may include the support 110, the mirror 120, a lens 130, an image sensor 140, and an analyzing unit 150.

The panel 200, which is an object to be inspected, is disposed on the support 110 that may be moved in at least one direction selected from an x direction, a y direction, and a z direction. In some example embodiments, the support 110 may be fixed and the lens 130 and the image sensor 140 may be moved.

The panel 200, which is an object to be inspected, may have various forms and functions. For example, the panel 200 may be a display panel, such as a liquid crystal display (LCD) panel, a light-emitting diode (LED) panel, or an organic light-emitting diode (OLED) panel. Alternatively, the panel 200 may include at least one curved portion. For example, the panel 200 may be a flexible panel or a flexible display panel. Accordingly, at least one portion thereof may be curved. Hereinafter, the panel 200 may refer to any type of panel that includes at least one curved portion.

Figure 8A:
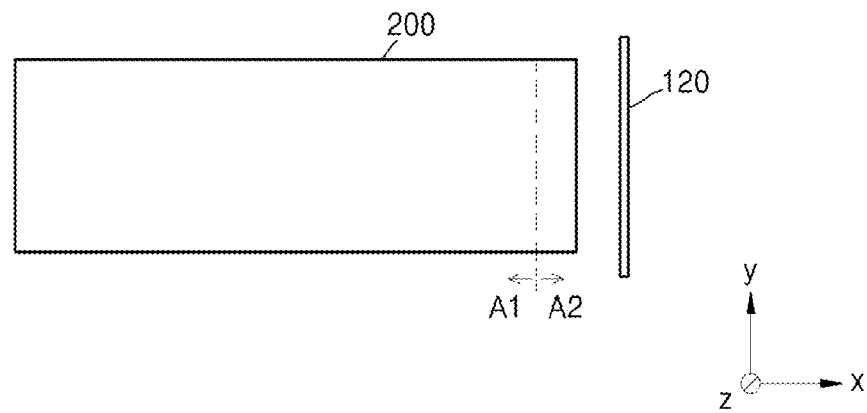
FIGS. 8A to 8C are conceptual views of positions of mirrors in panel inspecting apparatuses according to some example embodiments.
Figure 8B:
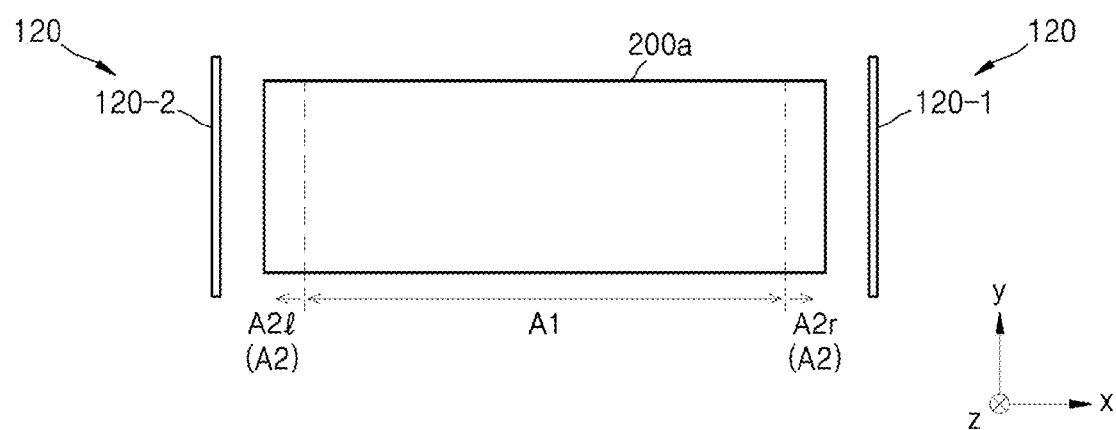
Figure 8C:
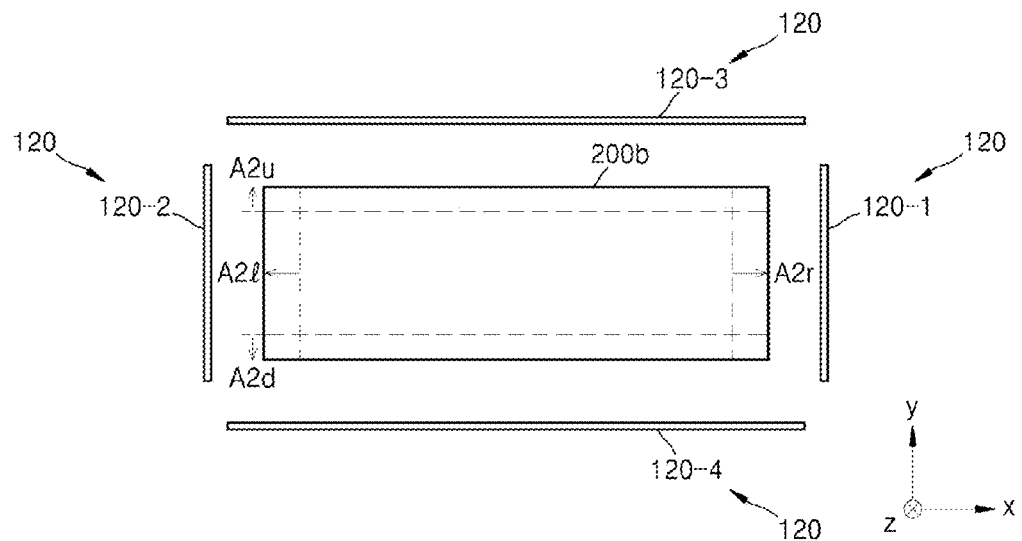

As shown in FIGS. 1A and 1B, the panel 200 may include a flat area A1 that is parallel to an upper surface of the support 110, and a curved area A2 that extends from the flat area A1 and is curved toward the support 110. The curved area A2 of the panel 200 may be disposed at an edge of the flat area A1 in a first direction (x direction) along a second direction (y direction). However, the curved area A2 may be disposed at various portions of the flat area A1, as shown in FIGS. 8A to 8C.

The panel 200, including the curved area A2, may be disposed on the support 110 by using a substrate 250 as a medium. The substrate 250 may include circuits for driving a thin film transistor (TFT) array in the panel 200. Also, an upper surface of the substrate 250 may be curved corresponding to the curved area A2 of the panel 200. In some example embodiments, instead of the substrate 250, a simple supporting component may be provided under the panel 200. In this case, the panel 200 may be electrically driven by being connected to a driver separate separately provided.

The mirror 120 may be a flat mirror. The mirror 120 may be disposed perpendicular to the panel 200. For example, a mirror surface MS of the mirror 120 may be disposed perpendicular to the upper surface of the support 110 or the flat area A1 of the panel 200. The mirror 120 may be disposed near the curved area A2 of the panel 200. As shown in the drawings, an image of the curved area A2 may be reflected by the mirror 120 and thus incident on the lens 130. A dash line at the right side of the mirror 120 indicates a virtual image VI.

By capturing the image of the curved area A2 of the panel 200 by using the reflection on the mirror 120, the image of the curved area A2 may be captured with uniform brightness and without pattern distortion. Brightness and pattern distortion of an image will be described in detail below with reference to FIGS. 4 and 5.

The lens 130 may receive an image from the panel 200 and an image reflected by the mirror 120, focus the images, and transfer the focused images to the image sensor 140. The image from the panel 200 is usually an image of the flat area A1, and the image reflected by the mirror 120 is usually an image of the curved area A2. According to some example embodiment, the image of the curved area A2 may be directly incident on the lens 130. In some example embodiments, the lens 130 may be disposed in the image sensor 140 as a portion of the image sensor 140.

The image sensor 140 may be a device that converts an image (or image information) received via the lens 130 to electric signals (digital information or image data). The image sensor 140 may be a Charge-Coupled Device (CCD) camera or a Complementary Metal-Oxide Semiconductor (CMOS) image sensor. In the panel inspecting apparatus 100 according to the present example embodiment, the image sensor 140 may be a CCD camera.

The CCD camera will be described. Light that is transmitted into a camera may be converted to electric signals by a CCD according to the intensity of the light. Then, the electric signals may be converted to an image file by an analog-digital converter (ADC), which converts analog signals to digital signals of 0 and 1, and the image file may be stored in a memory. In detail, when a shutter of the camera is pressed, light of an image may enter the CDD via a lens and a diaphragm, and then, light may be converted to electric signals by the CDD according to the intensity of the light. Light of the image that enters the CDD may be divided into different colors by an RGB color filter that is attached to the CDD. The divided colors may be converted to electric signals by hundreds of thousands of photosensitive devices that are included in the CDD. The performance of CCDs may be determined according to how many pixels (points forming an image) are included in an area. As the number of pixels included in an area increases, the sharpness of an image may increase. Image quality may be greatly affected by a degree of integration of the pixels, as well as a size of the CDD.

The analyzing unit 150 may receive image data or an image file from the image sensor 140, analyze the image data or the image file, and determine whether the panel 200 is defective based on the analysis result. For example, the analyzing unit 150 may use various analysis programs to analyze faulty pixels, distortion of a pattern (that is, a group of pixels), or non-uniform brightness of a pattern, and determine whether image quality of the panel 200 is defective according to a desired (or alternatively, predetermined) standard. The non-uniform brightness of the pattern may occur due to impurities inside a panel and include mura.

According to some example embodiments, the analysis result obtained by the analyzing unit 150 may be provided as feedback data for a panel manufacturing process and be used as data for analyzing reasons for defects and/or eliminating defects.

As described above, the panel 200 may be inspected to check whether image quality is normal or not. Problems stated below may occur when a curved portion of the panel 200 may be inspected by using an existing optical system for inspecting image quality of a flat display panel. For example, as light radiated from the curved portion deviates from a viewing angle of the optical system, brightness of light may become non-uniform. Also, due to a geometrical shape of the curved portion, the image sensor 140 may capture a distorted pattern. That is, the image sensor 140 may capture a distorted image. The non-uniform brightness and the pattern distortion of the curved portion of the panel 200 may become critical obstacles for accurately determining whether the curved portion is defective when the image quality of the panel 200 is inspected.

In order to solve the problems of, for example, the non-uniform brightness and the pattern distortion of the curved portion of the panel 200, an additional optical device may be desired. Because hundreds of image quality inspecting equipments are provided in an actual manufacturing line, if a unit image quality inspecting equipment have to include a plurality of optical systems or an optical system having a complicated structure, manufacturing and management cost or inspecting time may increase excessively.

The panel inspecting apparatus 100 according to the present example embodiment may solve the problems of the non-uniform brightness and the pattern distortion of the curved portion of the panel 200 by capturing an image of the curved area A2 by using the mirror 120 disposed near the curved area A2 of the panel 200. Accordingly, it may be accurately determined whether image quality of the curved area A2 of the panel 200 is defective.

Figure 2:
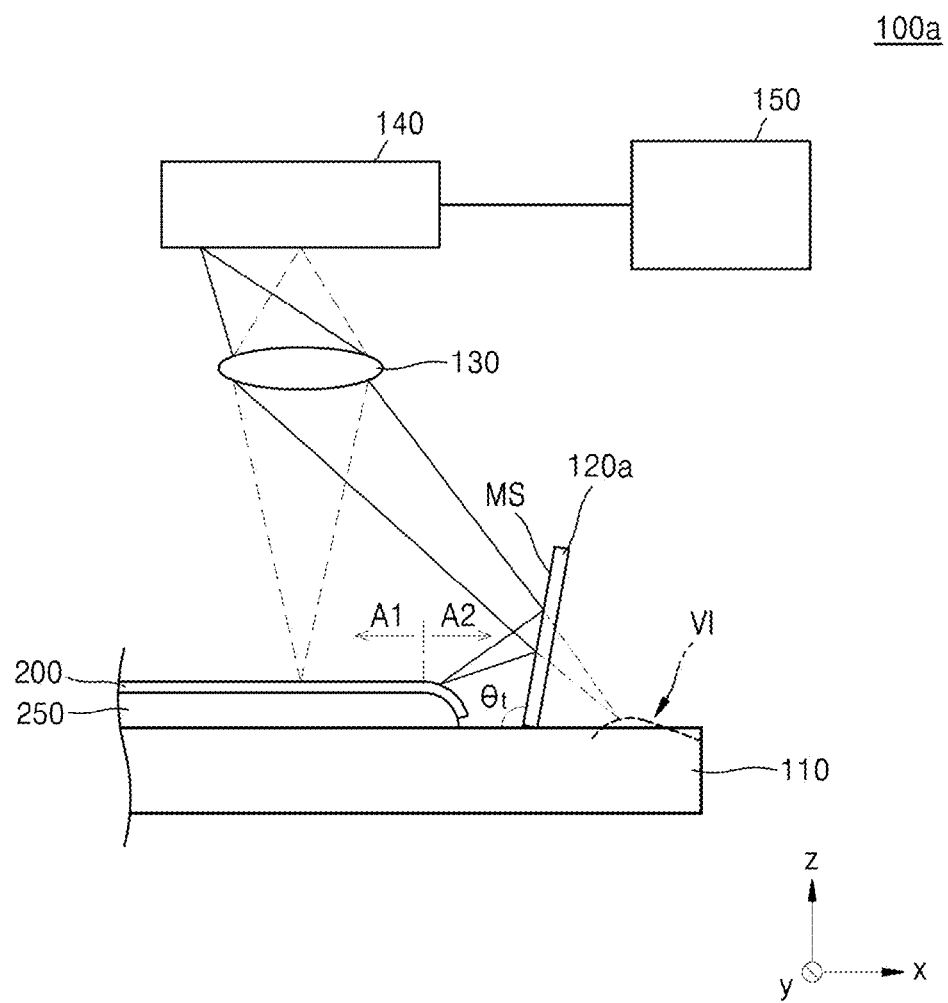
FIG. 2 is a conceptual view of a panel inspecting apparatus according to an example embodiment.

FIG. 2 is a conceptual view of a panel inspecting apparatus 100a according to an example embodiment. For convenience of description, features and elements described with reference to FIGS. 1A and 1B will be simply described or not be repeated.

Referring to FIG. 2, the panel inspecting apparatus 100a of the present example embodiment is similar to the panel inspecting apparatus 100 of FIG. 1, but may be different therefrom in that a mirror 120a is inclined at a desired (or alternatively, predetermined) angle with respect to the panel 200. For example, in the panel inspecting apparatus 100 of FIG. 1, the mirror 120 may be disposed such that the mirror surface MS is perpendicular to the flat area A1 of the panel 200. In the panel inspecting apparatus 100a according to the present example embodiment, the mirror 120a may be disposed such that a mirror surface MS is inclined at a first inclination angle $\theta_t$ with respect to the flat area A1 of the panel 200. The first inclination angle $\theta_t$ may be an obtuse angle. The first inclination angle $\theta_t$ may be determined based on uniform brightness and reducing pattern distortion of the curved area A2 of the panel 200: Also, the first inclination angle $\theta_t$ may be determined based on a viewing angle of the image sensor 140. Positions or characteristics of the lens 130 may be changed for the viewing angle of the image sensor 140.

For reference, when the viewing angle of the image sensor 140 is large, images that are incident at an oblique angle may be clearly captured. However, when the viewing angle is small, images that are incident at an oblique angle may be not clearly captured. Also, even when the viewing angle of the image sensor 140 is large, an image that is incident near a maximum viewing angle may be less sharp than an image that is perpendicularly incident, and thus may have pattern distortion.

Because the mirror 120a is disposed near the curved area A2 of the panel 200 and inclined at an obtuse angle, the image sensor 140 may obtain an image of the curved area A2 having uniform brightness and almost no pattern distortion. An inclination of the mirror 120a may be adjusted such that an optimal image of the curved area A2 of the panel 200 is incident on the lens 130. In other words, for uniform brightness and almost no pattern distortion in the image of the curved area A2, the inclination of the mirror 120a may be adjusted such that the image of the curved area A2 is incident at an angle that is relatively small with respect to the image sensor 140, and thus, an optimal image of the curved area A2 may be transferred to the image sensor 140 via the lens 130.

Hereinafter, for convenience of description, the support 110, the substrate 250, the image sensor 140, and the analyzing unit 150 will not be illustrated, and only an upper surface of the panel 200 will be illustrated. When a reflection of an image and a virtual image are described, the mirrors 120 and 120a are drawn using a thin line, and may refer to a flat mirror unless specified.

Figure 3:
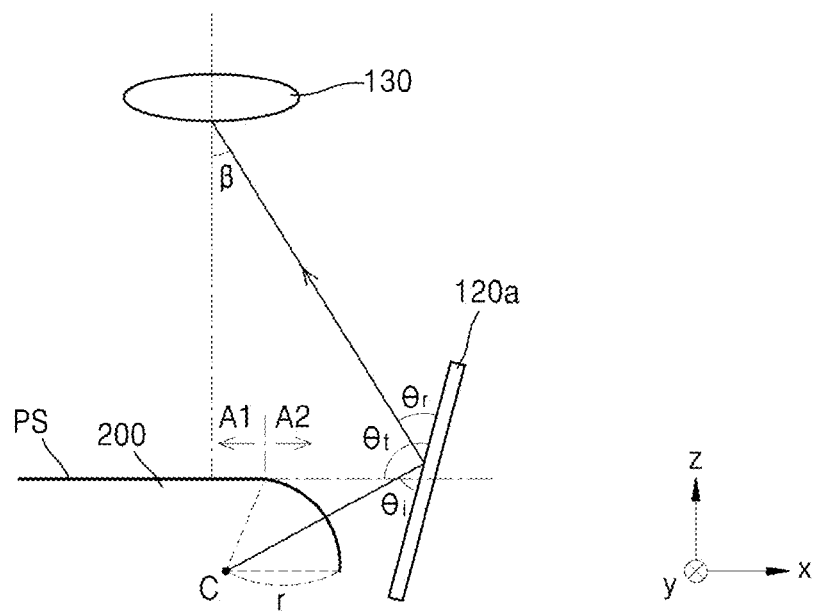
FIG. 3 is a conceptual view for describing an angle at which a mirror is disposed in the panel inspecting apparatus of FIG. 2.

FIG. 3 is a conceptual view for describing an angle at which the mirror 120a is disposed in the panel inspecting apparatus 100a of FIG. 2.

Referring to FIG. 3, the panel 200 may include the flat area A1 and the curved area A2. The curved area A2 may be formed as a circular arc having a first radius of curvature r. "C" may refer to a center of the circular arc having the first radius of curvature r. The curved area A2 may be formed as a circular arc having the first radius of curvature r and a central angle of 90° or less.

The curved area A2 of the panel 200 is not limited to a circular arc having a single radius of curvature. For example, the curved area A2 may be formed by combining a plurality of arcs that have different radii of curvatures. Also, the curved area A2 may not have a fixed radius of curvature.

The mirror 120a may be disposed such that the mirror 120a is inclined at the first inclination angle $\theta_t$ with respect to the panel 200. For example, the mirror 120a may be disposed at a side of the curved area A2 of the panel 200 such that the mirror surface MS of the mirror 120a and an upper surface PS of the panel 200 form the first inclination angle $\theta_t$. The first inclination angle $\theta_t$ may be, for example, an obtuse angle. Having the mirror 120a disposed as described above, the image of the curved area A2 may be incident on the lens 130 via the mirror 120a.

Reflection may be performed by the mirror 120a as follows: According to the law of reflection of a mirror, an incident angle of light incident on the mirror 120a is the same as a reflection angle of the light. An incident angle and a reflection angle are defined on a reflection plane (paper surface), on which light passes, and with respect to a line that is perpendicular to the mirror surface MS. When the incident angle is the same as the reflection angle, this may indicate that an angle $\theta_i$ at which light is incident with respect to the mirror surface MS is the same as an angle $\theta_r$ at which light is reflected with respect to the mirror surface MS. Therefore, instead of an incident angle and a reflection angle, the angles $\theta_i$ and $\theta_r$ with respect to the mirror surface MS are shown in FIG. 3 as well as the drawings thereafter.

The image of the curved area A2 reflected by the mirror 120a is incident on the lens 130 at a first incident angle $\beta$ with respect to a normal line of the lens 130. The first incident angle $\beta$ may be smaller than the viewing angle of the image sensor 140. Also, in order to obtain an image that is sharp and has no pattern distortion, the first inclination angle $\theta_t$ of the mirror 120a may be adjusted such that the first incident angle $\beta$ is reduced. In order to obtain an image of the curved area A2 having uniform brightness and no distortion, an angle at which the image of the curved area A2 is incident on the mirror 120a may also be considered. Therefore, the first inclination angle $\theta_t$ of the mirror 120a may need to be determined based on the angle at which the image of the curved area A2 is incident on the mirror 120a and the first incident angle $\beta$ at which the image is incident on the lens 130 by the reflection of the mirror 120a.

Figure 4A:
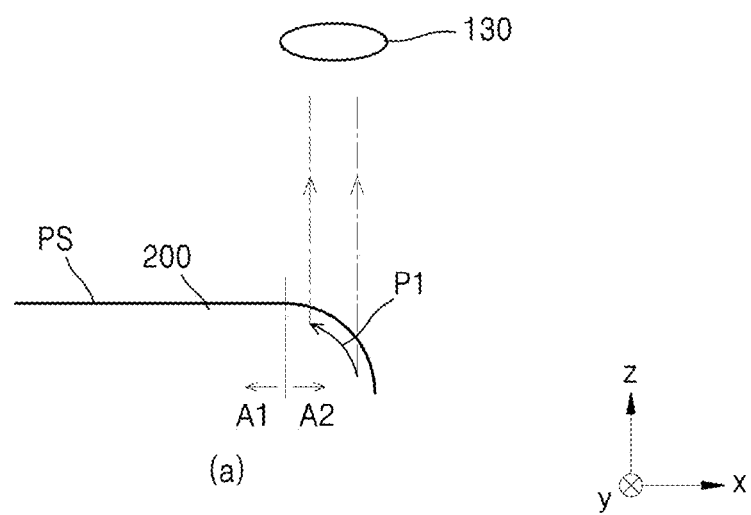
FIGS. 4A to 4C are conceptual views illustrating a principle of capturing an image of a pattern in a curved area of a panel.
Figure 4B:
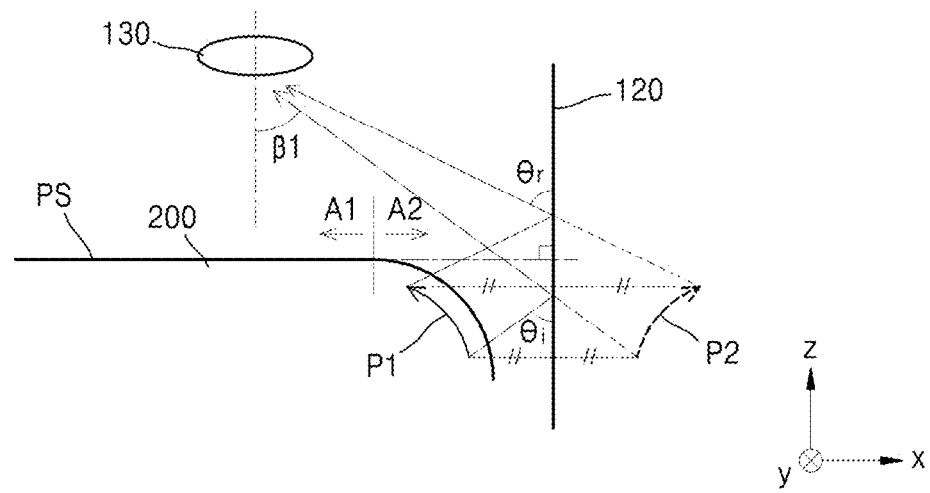
Figure 4C:
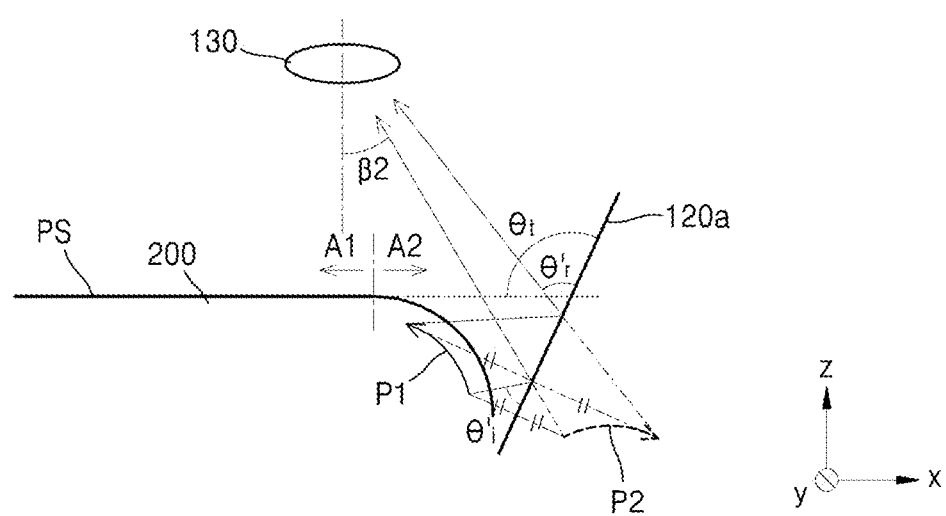

FIGS. 4A to 4C are conceptual views illustrating a principle of capturing an image of a pattern in a curved area of a panel. FIG. 4A shows an example without a mirror, FIG. 4B shows an example in which the mirror 120 is disposed perpendicular to a horizontal surface of the panel 200, and FIG. 4C shows an example in which the mirror 120a is disposed at an obtuse angle with respect to the horizontal surface of the panel 200.

Referring to FIG. 4A, when an image of a pattern P1 in the curved area A2, which is indicated by an arrow, is incident in a perpendicular direction (z direction) on the lens 130, a size of the image in a horizontal direction (x direction) may be decreased, and thus, pattern distortion may occur. Also, when light is uniformly spread in a radial shape on the curved area A2, only a portion of the light may be incident in the perpendicular direction on the lens 130. Therefore, the image of the pattern P1 obtained by the image sensor 140 may be relatively dark. For example, in the flat area A1, light on an image of a pattern may all be incident on the lens 130 because light proceeds in a perpendicular direction on the flat area A1. However, in the curved area A2, only a portion of light on the image of the pattern P1 may be incident on the lens 130, as described above. Therefore, the brightness of the image of the pattern P1 may be non-uniform in the curved area A2.

Referring to FIG. 4B, when the mirror 120 is disposed perpendicular to the panel 200, an image of the pattern P1 of the curved area A2 may be reflected by the mirror 120 and thus incident on the lens 130. Light of the image of the pattern P1 of the curved area A2 may be reflected by the mirror 120 at the incident and reflection angles $\theta_i$ and $\theta_r$, according to the law of reflection. Light that is reflected by the mirror 120 may be incident at a first incident angle $\beta 1$ on the lens 130. "P2", which is shown by a dash line, may refer to a virtual image formed on the mirror 120.

When the mirror 120 is perpendicular to the panel 200, the incident and reflection angles $\theta_i$ and $\theta_r$ may be large. In other words, light that is incident from the curved area A2 to the mirror 120 may have relatively small incident and reflection angles according to the general definition accepted in the field of science. Also, when light that is reflected by the mirror 120 is incident at the first incident angle β1 on the lens 130, the first incident angle β1 may be relatively large. As described above, when the incident and reflection angles $\theta_i$ and $\theta_r$ are large, the intensity of light that is incident on the mirror 120 per unit area may be increased, and thus, an image may become bright. However, when the first incident angle β1 toward the lens 130 is large, brightness may be decreased and pattern distortion may be enlarged.

Referring to FIG. 4C, when the mirror 120a is disposed at the first inclination angle $\theta_t$ with respect to the panel 200, incident and reflection angles $\theta_i'$ and $\theta_r'$ may be smaller than those when the mirror 120 is perpendicular to the panel 200. In other words, incident and reflection angles (according to the general definition accepted in the field of science) of light incident from the curved area A2 to the mirror 120a may be increased. Also, light that is reflected by the mirror 120a may be incident at a second incident angle β2 on the lens 130. The second incident angle β2 may be smaller than the first incident angle β1 of when the mirror 120 is perpendicular to the panel 200. When the incident and reflections angles $\theta_i'$ and $\theta_r'$ are small, the intensity of light that is incident on the mirror 120a per unit area may be decreased, and thus, an image may become relatively dark. However, because the second incident angle β2 toward the lens 130 is small, the intensity of light incident on the lens 130 may be large and pattern distortion may be relatively small.

As a result, the first inclination angle $\theta_t$ of the mirror 120a may be appropriately determined based on a change in brightness and distortion of an image reflected by the mirror 120 and a change in brightness and distortion of an image incident at the second incident angle β2 on the lens 130. In other words, the first inclination angle $\theta_t$ of the mirror 120a may be determined such that an optimal image of the curved area A2 is reflected by the mirror 120 and thus incident on the lens 130.

FIGS. 5A and 5B are photographs obtained by inspecting an image of a pattern in a curved area by a panel inspecting apparatus according to an example embodiment when a mirror is disposed perpendicularly and at an obtuse angle, respectively, with respect to the horizontal surface of a panel. FIG. 5A is a photograph obtained when the mirror is perpendicular to a horizontal surface of the panel, and FIG. 5B is a photograph obtained when the mirror is disposed at an obtuse angle with respect to the horizontal surface of the panel.

Referring to FIG. 5A, a pattern $P_{1P}$ of the flat area A1 may be shaped as a bright square. For example, a width of the pattern $P_{1P}$ in a first direction (x direction) may be a first width W1. On the other hand, a pattern $P_{1C}$ of the curved area A2 may have a rectangular shape and be darker than the pattern $P_{1P}$ of the flat area A1. For example, a width of the pattern $P_{1C}$ of the curved area A2 in the first direction may be a second width W2 that is smaller than the first width W1.

In the panel 200, the pattern $P_{1P}$ of the flat area A1 and the pattern $P_{1C}$ of the curved area A2 have the same width in the first direction. However, as shown in FIG. 5A, an image of a pattern measured by the image sensor 140 may be completely different in the flat area A1 and the curved area A2. For example, an image of the pattern $P_{1C}$ of the curved area A2 may be distorted and darker than an image of an actual pattern.

Based on a white dash line across the photograph in the y direction, the upper portion is a photograph obtained by measuring a real image RI and the lower portion is an image of a mirror, that is, a photograph obtained by measuring a virtual image VI. Also, the white dash line may indicate a position of a mirror. Therefore, a pattern $P_2$ that is obtained by the mirror 120 perpendicular to the panel 200 is based on the virtual image VI. A width of the pattern $P_2$ in the first direction may be a third width W3 that may be smaller than the first width W1 but larger than the second width W2. The pattern $P_2$ may still be dark because an image reflected by the mirror 120 is incident at a relatively large incident angle on the lens 130.

Referring to the photograph of FIG. 5B, a pattern $P_{1P}$ of the flat area A1 and a pattern $P_{1C}$ of the curved area A2 may be the same as the patterns $P_{1P}$ and $P_{1C}$ in the photograph of FIG. 5A. In the photograph of FIG. 5B also, based on the white dash line, the upper portion may be a photograph of a real image RI and the lower portion may be a photograph of a virtual image VI. A pattern $P_2'$ is obtained by the mirror 120a that is disposed at an inclination angle with respect to the panel 200. A width of the pattern $P_2'$ in the first direction may be a third width W3' that may be larger than the second width W2. The third width W3' may be slightly smaller than the first width W1 but almost the same as the first width W1. Therefore, the pattern $P_2'$ obtained by the mirror 120a may have a substantially reduced distortion.

The pattern $P_2'$ obtained by the mirror 120a may be darker than the pattern $P_{1P}$ of the flat area A1 but brighter than the pattern $P_{1C}$ of the curved area A2. As a result, by disposing the mirror 120a at an appropriate inclination angle with respect to the panel 200, an image of the curved area A2 may be obtained, the image of which pattern distortion may be reduced and brightness may be increased. Therefore, when the image quality of the panel 200 is inspected for the image quality, it may be accurately determined whether the curved area A2 is defective.

Figure 6:
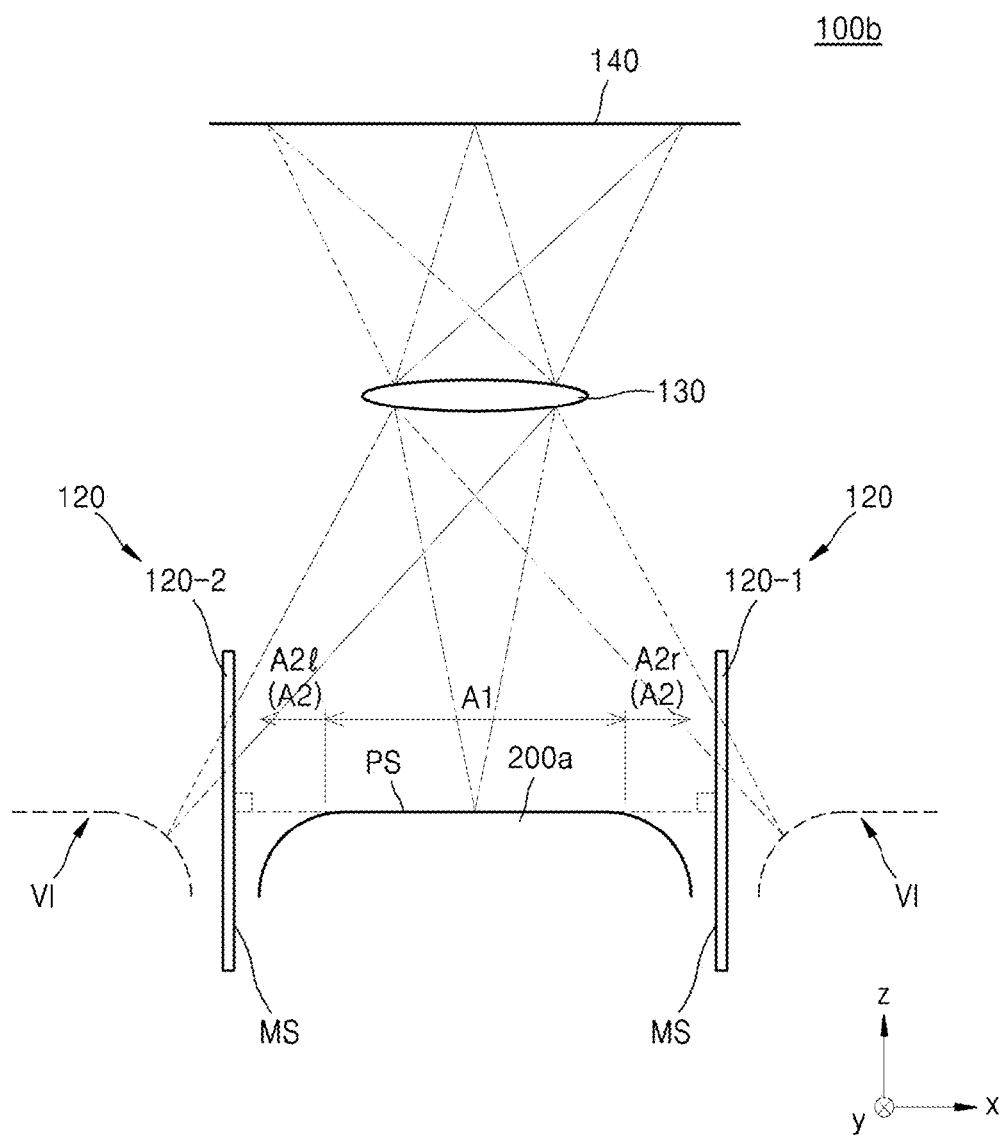
FIGS. 6 and 7 are conceptual views of a panel inspecting apparatus according to some example embodiment.
Figure 7:
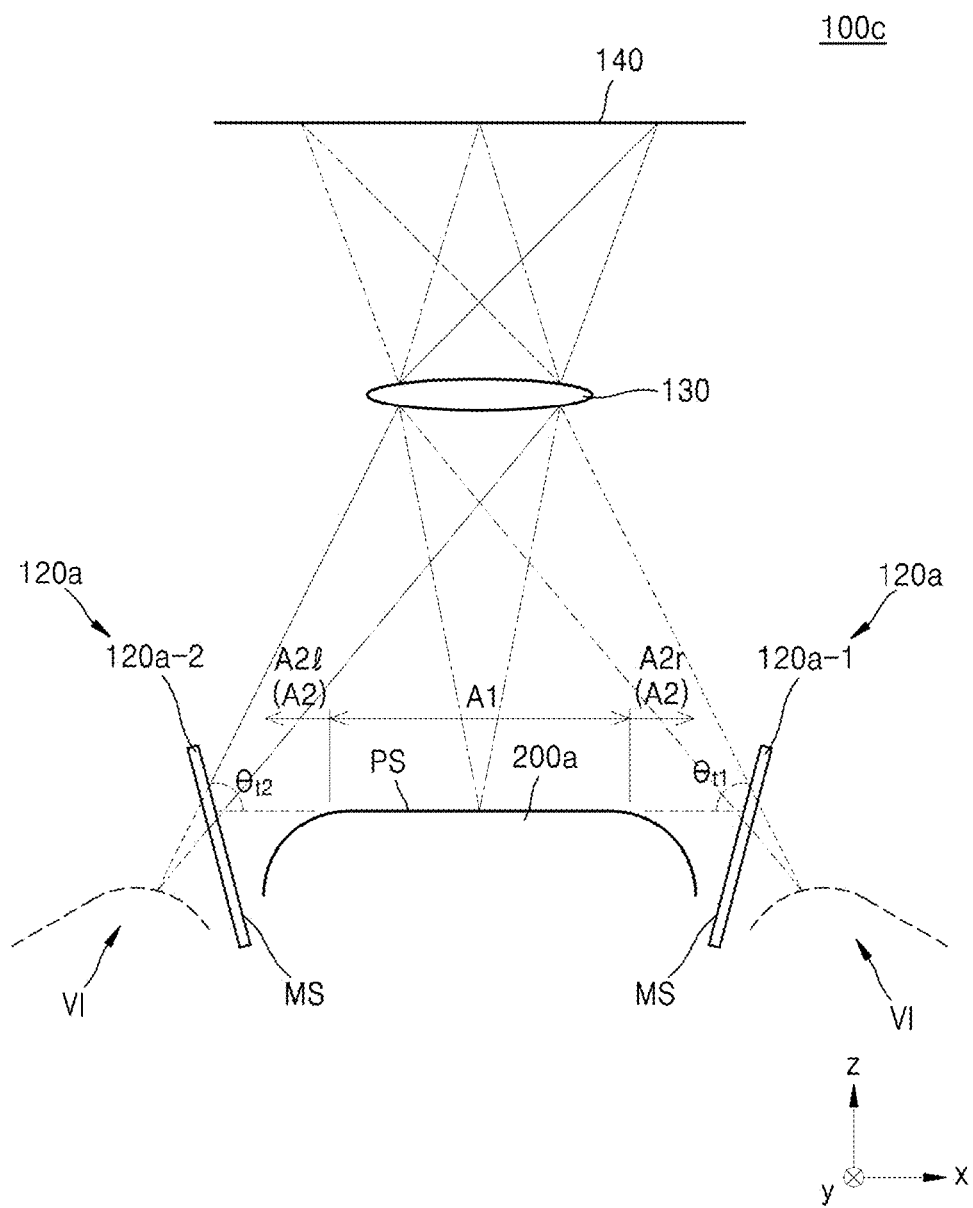

FIGS. 6 and 7 are conceptual views of panel inspecting apparatuses 100b and 100c according to some example embodiments. For convenience of description, features and elements described with reference to FIGS. 1A and 2 will be simply described or not be repeated.

Referring to FIG. 6, the panel inspecting apparatus 100b according to the present example embodiment may include two mirrors 120. For example, the two mirrors 120 may include a first mirror 120-1 disposed at the right side of a panel 200a and a second mirror 120-2 disposed at the left side of the panel 200a.

The panel 200a may include curved areas A2 along a second direction (y direction) at both edges of the panel 200a in a first direction (x direction). For example, the curved areas A2 may include a right curved area A2r disposed at the right edge of the panel 200a and a left curved area A21 disposed at the left edge of the panel 200a. A flat area A1 may be disposed between the right curved area A2r and the left curved area A21. The right curved area A2r and the left curved area A21 may have the same or different shapes. For example, the right curved area A2r may have a first radius of curvature, whereas the left curved area A21 may have a second radius of curvature that is different from the first radius of curvature of the right curved area A2r.

When the panel 200a includes two curved areas A2, the two mirrors 120 corresponding to the two curved areas A2 may be disposed. For example, the first mirror 120-1 may be disposed corresponding to the right curved area A2r, and the second mirror 120-2 may be disposed corresponding to the left curved area A21. The first mirror 120-1 and the second mirror 120-2 may be perpendicular to the panel 200a. For example, the first mirror 120-1 and the second mirror 120-2 may be perpendicular to an upper surface PS of the panel

200*a*. The first mirror 120-1 and the second mirror 120-2 may be disposed such that mirror surfaces MS thereof face each other.

As shown in FIG. 6, the panel inspecting apparatus 100*b* according to the present example embodiment may include a single lens 130 and a single image sensor 140 corresponding to the lens 130. In this structure, an image of the right curved area A2*r* may be reflected by the first mirror 120-1 and thus incident on the lens 130, and an image of the left curved area A2*l* may be reflected by the second mirror 120-2 and thus incident on the lens 130. The two mirrors 120 may be respectively disposed near the curved areas A2 so that the images reflected by the two mirrors 120 are incident on the single lens 130. Dash lines on the right side of the first mirror 120-1 and the left side of the second mirror 120-2 indicate virtual images VI of the panel 200*a*.

Referring to FIG. 7, the panel inspecting apparatus 100*c* according to the present example embodiment may be similar to the panel inspecting apparatus 100*b* of FIG. 6 in that two mirrors 120*a* are included. However, unlike the panel inspecting apparatus 100*b* of FIG. 6, the two mirrors 120*a* may be inclined with respect to the panel 200*a*.

For example, the two mirrors 120*a* may include a first mirror 120*a*-1 disposed at the right side of the panel 200*a* and a second mirror 120*a*-2 disposed at the left side of the panel 200*a*. The first mirror 120*a*-1 may be disposed corresponding to the right curved area A2*r* of the panel 200*a* and form a first inclination angle $\theta_{t1}$ with the panel 200*a*. The second mirror 120*a*-2 may be disposed corresponding to the left curved area A2*l* of the panel 200*a* and form a second inclination angle $\theta_{t2}$ with the panel 200*a*.

When the right curved area A2*r* has the same radius of curvature as the left curved area A2*l* of the panel 200*a*, the first inclination angle $\theta_{t1}$ of the first mirror 120*a*-1 may be the same as the second inclination angle $\theta_{t2}$ of the second mirror 120*a*-2. Alternatively, even when the right curved area A2*r* has the same radius of curvature as that of the left curved area A2*l*, the first mirror 120*a*-1 may have a different inclination angle than that of the second mirror 120*a*-2. When the right curved area A2*r* has a different radius of curvature than that of the left curved area A2*l*, the first inclination angle $\theta_{t1}$ of the first mirror 120*a*-1 may be different than the second inclination angle $\theta_{t2}$ of the second mirror 120*a*-2. However, the present example embodiment is not limited thereto, and the first mirror 120*a*-1 may have the same inclination angle as the second mirror 120*a*-2.

Because the panel inspecting apparatus 100*c* according to the present example embodiment includes the single lens 130, taking into account an angle at which images reflected by the mirror 120*a* are incident on the lens 130, the first and second inclination angles $\theta_{t1}$ and $\theta_{t2}$ of the first and second mirrors 120*a*-1 and 120*a*-2 may be adjusted. Dash lines on the right side of the first mirror 120*a*-1 and the left side of the second mirror 120*a*-2 may also indicate virtual images VI of the panel 200*a*.

FIGS. 8A to 8C are conceptual views of positions of mirrors in panel inspecting apparatuses according to some example embodiments.

Referring to FIG. 8A, the panel 200 may include one curved area A2 at one end of the first direction (x direction), as shown in FIG. 1A, 1B, or 2. In this structure of the panel 200, only one mirror 120 may be disposed corresponding to the curved area A2.

The mirror 120 may be disposed perpendicular to the panel 200, as shown in FIG. 1A, or disposed such that an obtuse inclination angle is formed with the panel 200, as shown in FIG. 2. In order to completely cover the curved area A2, a width of the mirror 120 in the second direction (y direction) may be larger than a width of the curved area A2 in the second direction. However, the present example embodiment is not limited thereto, and the width of the mirror 120 in the second direction (y direction) may be smaller than the width of the curved area A2 in the second direction. Also, as shown in FIG. 1A or 2, a height of the mirror 120 in a third direction (z direction) may be greater than a height of the curved area A2 in the third direction.

Referring to FIG. 8B, the panel 200*a* may include two curved areas A2 at both edges thereof in the first direction (x direction), as shown in FIG. 6 or 7. That is, the curved areas A2 may include the right curved area A2*r* and the left curved area A2*l*. In this structure of the panel 200*a*, two mirrors 120 may be disposed corresponding to the two curved areas A2, respectively. For example, the first mirror 120-1 may be disposed corresponding to the right curved area A2*r*, and the second mirror 120-2 may be disposed corresponding to the left curved area A2*l*.

The first mirror 120-1 and the second mirror 120-2 may be disposed perpendicular to the panel 200*a* or disposed such that an obtuse inclination angle is formed with respect to the panel 200*a*. When the first mirror 120-1 and the second mirror 120-2 are disposed perpendicularly, respective mirror surfaces of the first mirror 120-1 and the second mirror 120-2 may face each other. When the first mirror 120-1 and the second mirror 120-2 form an obtuse inclination angle with the panel 200*a*, the first mirror 120-1 and the second mirror 120-2 may have the same or different inclination angles. Respective sizes of the first mirror 120-1 and the second mirror 120-2 may be the same as described with reference to FIG. 8A.

Referring to FIG. 8C, a panel 200*b* may include two curved areas A2 at both edges thereof in the first direction (x direction) and two curved areas A2 at both edges thereof in the second direction (y direction). That is, the curved areas A2 may include the right curved area A2*r* and the left curved area A2*l* at the both edges thereof in the first direction, and an upper curved area A2*u* and a lower curved area A2*d* at the both edges thereof in the second direction. In this structure of the panel 200*b*, four mirrors 120 may be disposed corresponding to the four curved areas A2. For example, the first mirror 120-1 may be disposed corresponding to the right curved area A2*r*, the second mirror 120-2 may be disposed corresponding to the left curved area A2*l*, a third mirror 120-3 may be disposed corresponding to the upper curved area A2*u*, and a fourth mirror 120-4 may be disposed corresponding to lower curved area A2*d*.

The first to fourth mirrors 120-1 to 120-4 may be disposed perpendicular to the panel 200*b* or disposed such that an obtuse inclination angle is formed with respect to the panel 200*b*. When the first to fourth mirrors 120-1 to 120-4 are disposed perpendicularly, respective mirror surfaces of the first mirror 120-1 and the second mirror 120-2 may face each other, and respective mirror surfaces of the third mirror 120-3 and the fourth mirror 120-4 may face each other. When the first to fourth mirrors 120-1 to 120-4 form an obtuse inclination angle with respect to the panel 200*b*, respective inclination angles of the first to fourth mirrors 120-1 to 120-4 may be the same as each other. When the first to fourth mirrors 120-1 to 120-4 form an obtuse inclination angle with the panel 200*b*, an inclination angle of at least one mirror may be different from inclination angles of other mirrors.

Respective sizes of the first mirror 120-1 and the second mirror 120-2 are the same as described with reference to FIG. 8A. Respective sizes of the third mirror 120-3 and the fourth mirror 120-4 may correspond to the upper curved area A2u and the lower curved area A2d of the panel 200b. For example, in order to completely cover the upper curved area A2u, a width of the third mirror 120-3 in the first direction may be greater than a width of the upper curved area A2u in the first direction. As shown in FIG. 1A or 2, a height of the third mirror 120-3 in the third direction (z direction) may be greater than a height of the upper curved area A2u in the third direction. A size of the fourth mirror 120-4 may be the same as that of the third mirror 120-3.

Although examples of inspecting a panel having a rectangular horizontal surface are described above, a panel inspecting apparatus according to the present example embodiment is not limited to inspecting a rectangular panel. For example, a horizontal surface of a panel may have shapes other than a rectangle, for example, a polygon, a circle, or an oval. Also, at least a portion of the panel may be a curved area. When the panel having such structure is inspected, the panel inspecting apparatus according to the present example embodiment may include a mirror having an appropriate size and an inclination angle with respect to a curved area of the panel so that image quality of the curved area of the panel may be conveniently and accurately inspected.

Figure 9:
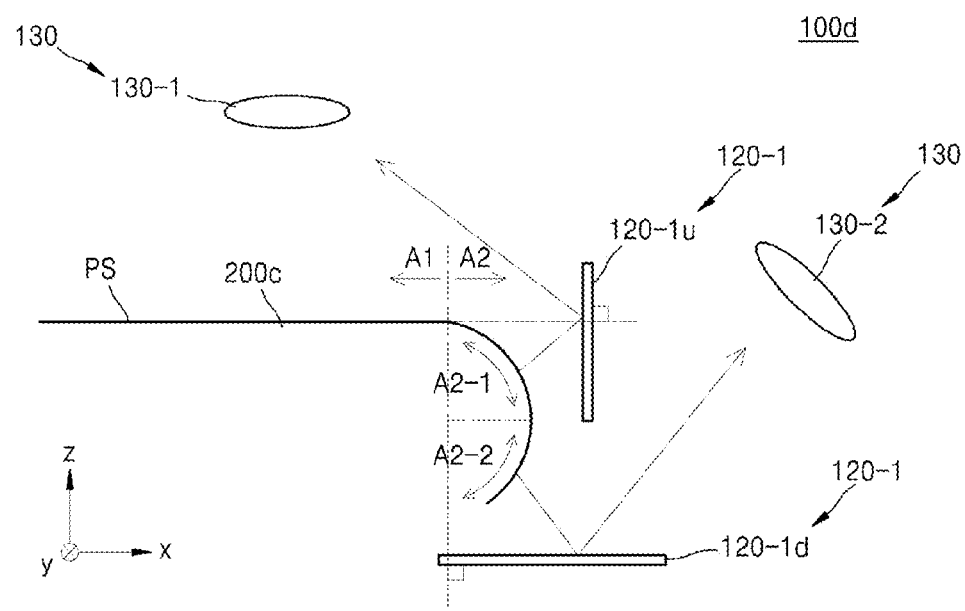
FIG. 9 is a conceptual view of a panel inspecting apparatus according to an example embodiment.

FIG. 9 is a conceptual view of a panel inspecting apparatus 100d according to an example embodiment.

Referring to FIG. 9, the panel inspecting apparatus 100d according to the present example embodiment may include two first mirrors 120-1 to capture a single image of a curved area A2. Further, the panel inspecting apparatus 100d may include two lenses 130 that correspond to the two first mirrors 120-1, respectively.

For example, the curved area A2 of a panel 200c may be shaped as a circular arc that has a central angle of 90° or more, unlike the panel 200 of FIGS. 1A, 1B, and 2. Accordingly, the curved area A2 may be distinguished as a first curved area A2-1 at an upper portion and a second curved area A2-2 at a lower portion. Features and shapes of the first curved area A2-1 and the second curved area A2-2 will be described in detail with reference to FIGS. 10A and 10C.

When the curved area A2 of the panel 200c is shaped as described above, the second curved area A2-2 may not be examined by using an existing optical system for inspecting image quality of a flat display panel. Further, an image of the curved area A2 may not be fully covered by using only one mirror. Accordingly, the panel inspecting apparatus 100d according to the present example embodiment may have two mirrors to completely cover the curved area A2. For example, the two first mirrors 120-1 may include a first upper mirror 120-1u and a first lower mirror 120-1d. The first upper mirror 120-1u may be disposed corresponding to the first curved area A2-1, and the first lower mirror 120-1d may be disposed corresponding to the second curved area A2-2.

As shown in FIG. 9, the first upper mirror 120-1u may be disposed perpendicular to an upper surface PS of the panel 200c. Also, the first lower mirror 120-1d may be disposed in parallel to the upper surface PS of the panel 200c. Supposing that the second curved area A2-2 is similar to the first curved area A2-1, the first lower mirror 120-1d may be regarded as being disposed perpendicular to a vertical surface of the panel 200c.

The two lenses 130 include a first lens 130-1 and a second lens 130-2. An image of the first curved area A2-1 may be transferred to the first lens 130-1 by being reflected by the first upper mirror 120-1u, and an image of the second curved area A2-2 may be transferred to the second lens 130-2 by being reflected by the first lower mirror 120-1d. The first lens 130-1 may be disposed at an optimal location for receiving an image of a flat area A1 and the image of the first curved area A2-1 which are reflected by the first upper mirror 120-1u. Also, in order to effectively transfer the image of the first curved area A2-1 to the first lens 130-1 by reflecting the image on the first upper mirror 120-1u, the first upper mirror 120-1u may be disposed near the first curved area A2-1. The second lens 130-2 may be disposed at an optimal location for receiving the image of the second curved area A2-2 that is reflected by the first lower mirror 120-1d. Based on respective locations of the first upper mirror 120-1u and the first lower mirror 120-1d, the first lens 130-1 may be disposed in a different direction than that of the second lens 130-2.

In general, when a panel inspecting apparatus includes a plurality of lenses, the panel inspecting apparatus may include a plurality of image sensors (140 of FIG. 1) corresponding to the plurality of lenses. Therefore, the panel inspecting apparatus 100d according to the present example embodiment may include two image sensors corresponding to the two lenses 130. Even when a plurality of lenses are included, the number of image sensors included in the panel inspecting apparatus may be less than the number of lenses. For example, one image sensor may be included in the panel inspecting apparatus.

Even when a curved area of a panel, which is an object for inspecting, is shaped as a circular arc having a central angle of at least 90°, the panel inspecting apparatus 100d according to the present example embodiment may conveniently and accurately inspect image quality of the curved area of the panel by using two mirrors.

Figure 10A:
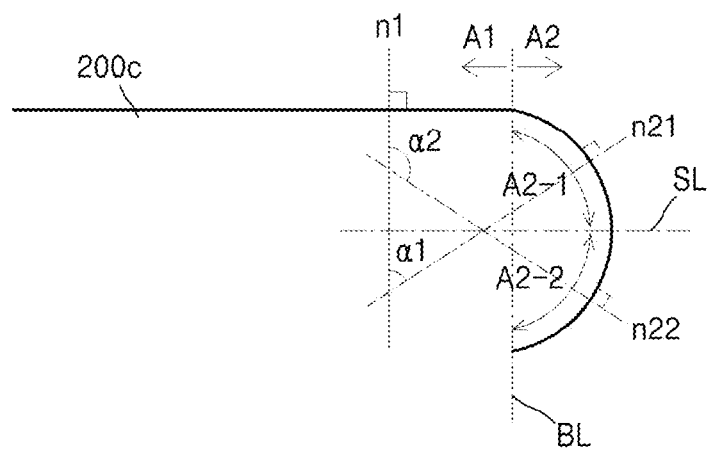
FIGS. 10A to 10C are cross-sectional views of a curved area of a panel to be inspected by the panel inspecting apparatus of FIG. 9.
Figure 10B:
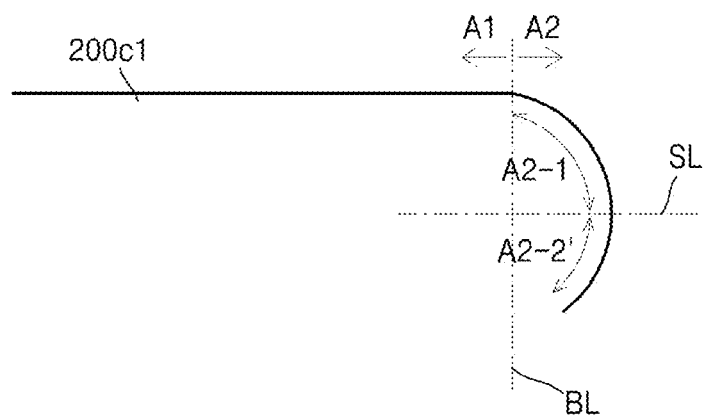
Figure 10C:
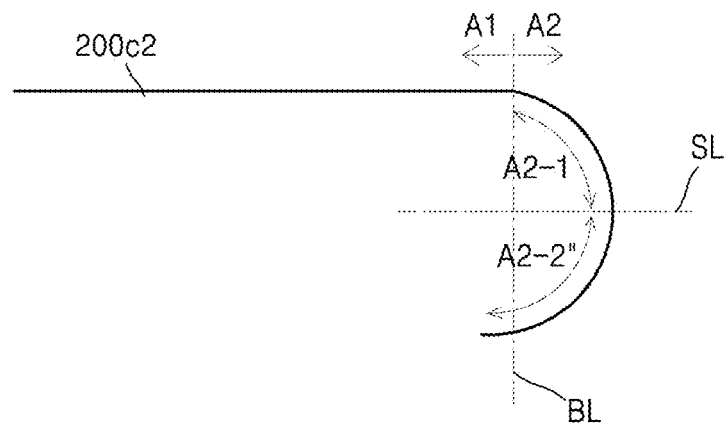

FIGS. 10A to 10C are cross-sectional views of a curved area of a panel to be inspected by the panel inspecting apparatus 100d of FIG. 9.

Referring to FIG. 10a, the curved area A2 of the panel 200c may be distinguished as the first curved area A2-1 and the second curved area A2-2. The first curved area A2-1 may be distinguished from the second curved area A2-2 by using the following methods.

For example, in FIG. 10a, when a normal line of the flat area A1 is referred to as a first normal line n1, a second normal line n21 that is a normal line of the first curved area A2-1 may form an acute angle with the first normal line n1, and a third normal line n22 that is a normal line of the second curved area A2-2 may form an obtuse angle with the first normal line n1. The acute angle and the obtuse angle may indicate angles between normal lines in an outer direction of the panel 200c. Therefore, a range in which a normal line of the curved area A2 forms an acute angle with the first normal line n1 may be defined as the first curved area A2-1, and a range in which a normal line of the curved area A2 forms an obtuse angle with the first normal line n1 may be defined as the second curved area A2-2.

When respective radii of curvatures of the first and second curved areas A2-1 and A2-2 are the same as each other, based on an side of the flat area A1, a portion of the curved area A2 of which a central angle is 90° or less may be defined as the first curved area A2-1, and a portion of the curved area A2 of which a central angle is more than 90° may be defined as the second curved area A2-2. When the first curved area A2-1 and the second curved area A2-2 are symmetric about a central line SL, the upper area of the curved area A2 with respect to the central line SL may be defined as the first curved area A2-1 and the lower area of the curved area A2 with respect to the central line SL may be defined as the second curved area A2-2. When the curved area A2 of the panel 200c does not have a constant radius of curvature, the first curved area A2-1 may generally be distinguished from the second curved area A2-2 by using the idea of normal lines.

Referring to FIG. 10B, a curved area A2 of a panel 200c1 may be shaped differently from the curved area A2 of the panel 200c of FIG. 10A. For example, in FIG. 10A, the second curved area A2-2 is symmetric with the first curved area A2-1 about the central line SL, and accordingly, a lower edge of the second curved area A2-2 may contact a boundary line BL between the flat area A1 and the curved area A2. However, in the curved area A2 of the panel 200c1, a second curved area A2-2' may not be symmetric with a first curved area A2-1 about a central line SL and may only be partially formed. Therefore, a lower edge of the second curved area A2-2' may not extend to a boundary line BL between the flat area A1 and the curved area A2.

Referring to FIG. 10C, a curved area A2 of a panel 200c2 may be shaped differently from the curved area A2 of the panel 200c of FIG. 10A. For example, in the curved area A2 of the panel 200c2, a second curved area A2-2" may be not symmetric with a first curved area A2-1 about a central line SL and may be larger than the first curved area A2-1. Therefore, a lower edge of the second curved area A2-2" may extend over a boundary line BL between a flat area A1 and the curved area A2.

A portion of the second curved area A2-2", which extends over the boundary line BL, may have the same radius of curvature as other portions of the second curved area A2-2". Further, the portion of the second curved area A2-2", which extends over the boundary line BL, may be flat and parallel to the flat area A1.

FIGS. 11 to 14 are conceptual views of panel inspecting apparatuses 100e, 100f 100g, and 100h according to some example embodiments. For convenience of description features and elements described with reference to FIG. 9 will be simply described or not be repeated.

Figure 11:
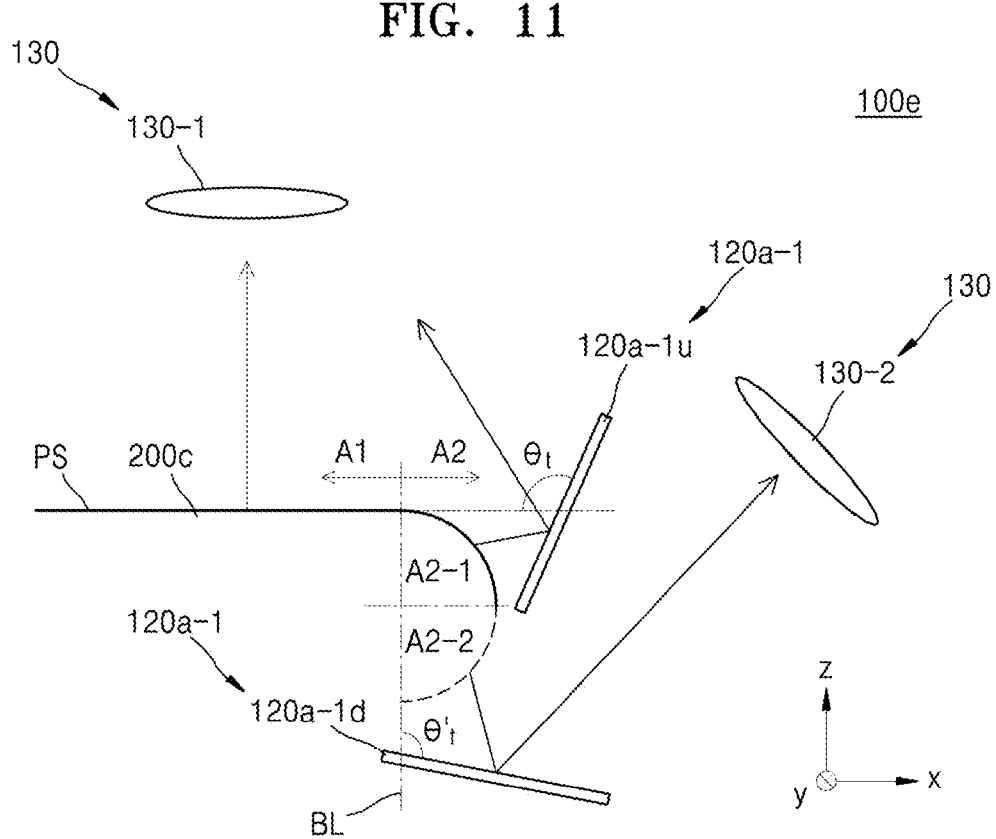
FIGS. 11 to 14 are conceptual views of panel inspecting apparatuses according to some example embodiments.

Referring to FIG. 11, the panel inspecting apparatus 100e according to the present example embodiment may include two first mirrors 120a-1 and two lenses 130, similarly to the panel inspecting apparatus 100d of FIG. 9. However, in the panel inspecting apparatus 100e according to the present example embodiment, the two first mirrors 120a-1 may be relatively more inclined with respect to the panel 200c.

For example, the two first mirrors 120a-1 may include a first upper mirror 120a-1u and a first lower mirror 120a-1d. The first upper mirror 120a-1u may be disposed at a first inclination angle $\theta_t$ with respect to the upper surface PS of the panel 200c. The first inclination angle $\theta_t$ may be, for example, an obtuse angle. When a boundary line BL between the flat area A1 and the curved area A2 correspond to a vertical surface of the panel 200c, the first lower mirror 120a-1d may be disposed at a second inclination angle $\theta_t'$ with respect to the vertical surface of the panel 200c. The first inclination angle $\theta_t$ may be the same as or different than the second inclination angle $\theta_t'$.

As described with reference to FIG. 9, the two lenses 130 may include the first lens 130-1 and the second lens 130-2. An image of the first curved area A2-1 may be reflected by the first upper mirror 120a-1u and thus transferred to the first lens 130-1, and an image of the second curved area A2-2 may be reflected by the first lower mirror 120a-1d and thus transferred to the second lens 130-2. Respective positions of the first lens 130-1 and the second lens 130-2 are the same as described above with reference to FIG. 9. However, because the first inclination angle $\theta_t$ of the first upper mirror 120a-1u and the second inclination angle $\theta_t'$ of the first lower mirror 120a-1d may be adjusted, the image of the first curved area A2-1 and the image of the second curved area A2-2 may be optimized by adjusting the first inclination angle $\theta_t$ of the first upper mirror 120a-1u and the second inclination angle $\theta_t'$ of the first lower mirror 120a-1d instead of adjusting the respective positions of the first lens 130-1 and the second lens 130-2.

Figure 12:
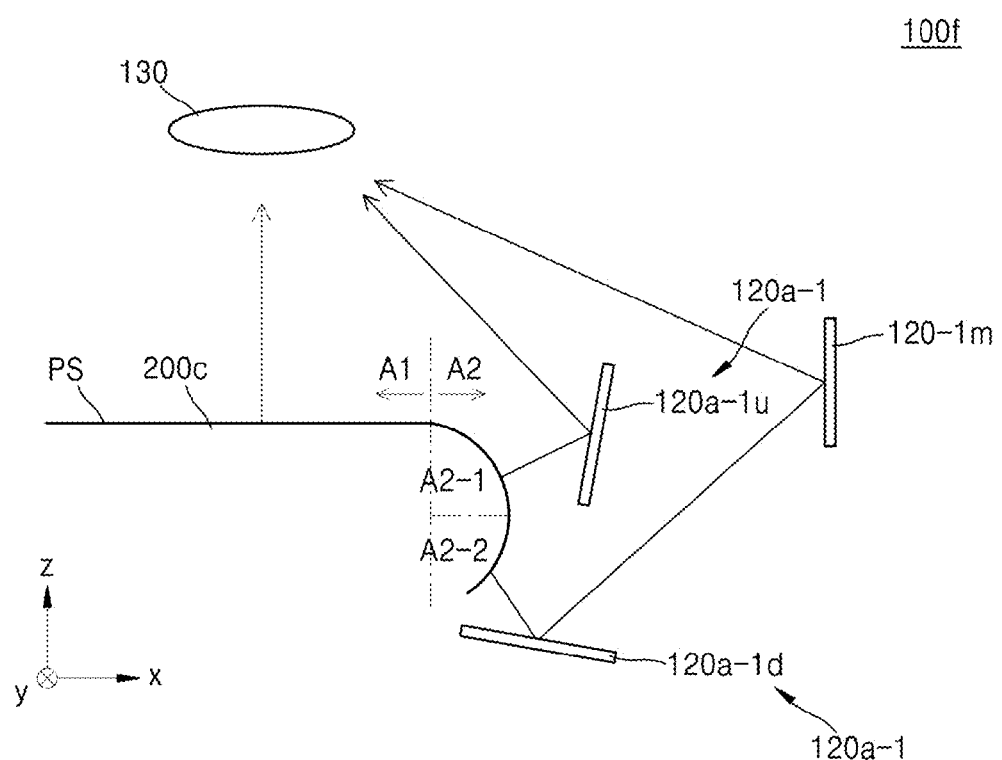

Referring to FIG. 12, the panel inspecting apparatus 100f according to the present example embodiment may be similar to the panel inspecting apparatus 100e of FIG. 11 in that two first mirrors 120a-1 are included. However, the panel inspecting apparatus 100f according to the present example embodiment may be different from the panel inspecting apparatus 100e of FIG. 11 in that a medium mirror 120-1m is included instead of the second lens 130-2.

For example, the two first mirrors 120a-1 may include the first upper mirror 120a-1u and the first lower mirror 120a-1d. The medium mirror 120-1m may be perpendicular to the panel 200c and may transfer an image, which is reflected by the first lower mirror 120a-1d, to the lens 130. The medium mirror 120-1m may be inclined with respect to the panel 200c. For example, the medium mirror 120-1m may be disposed at an inclination angle that may effectively reflect an image reflected by the first lower mirror 120a-1d and transfer the image to a lens 130 at an optimal incident angle. Thus, an inclination angle of the medium mirror 120-1m may be determined based on an inclination angle of the first lower mirror 120a-1d, and an incident angle of the medium mirror 120-1m, and an angle at which an image is incident on the lens 130. The panel inspecting apparatus 100f according to the present example embodiment may include only one lens 130 by including the medium mirror 120-1m, and include only one image sensor. Therefore, the panel inspecting apparatus 100f of the present example embodiment may simplify a structure of an entire inspecting apparatus.

Figure 13:
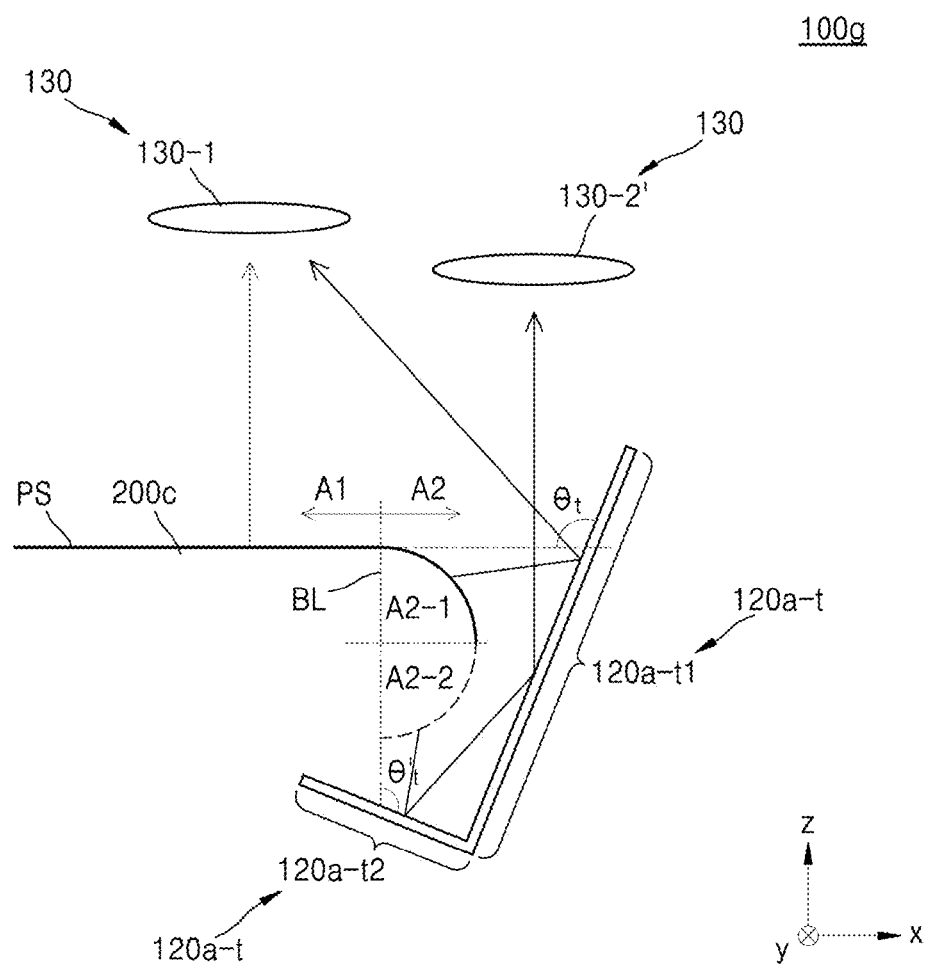

Referring to FIG. 13, the panel inspecting apparatus 100g according to the present example embodiment may include a combination mirror 120a-t and two lenses 130. A perpendicular cross-section of the combination mirror 120a-t may be shaped as an "L." However, the perpendicular cross-section of the combination mirror 120a-t is not limited thereto.

The combination mirror 120a-t may include a first portion 120a-t1 and a second portion 120a-t2. The first portion 120a-t1 and the second portion 120a-t2 may be perpendicularly coupled to each other. However, a coupling angle between the first and second portions 120a-t1 and 120a-t2 is not limited to 90°. For example, the first portion 120a-t1 and the second portion 120a-t2 may be coupled at an acute angle or an obtuse angle.

The first portion 120a-t1 may correspond to the first curved area A2-1 of the panel 200c, and the second portion 120a-t2 may correspond to the second curved area A2-2 of the panel 200c. As shown in FIG. 13, with the second portion 120a-t2, the first portion 120a-t1 may contribute to reflecting an image of the second curved area A2-2. According to some example embodiments, the image of the second curved area A2-2 may be transferred to the lens 130 by only being reflected by the second portion 120a-t2 without being reflected by the first portion 120a-t1.

Similar to the first upper mirror 120a-1u, the first portion 120a-t1 may form a first inclination angle $\theta_t$ with the upper surface PS of the panel 200c. Also, the second portion 120a-t2 may form a second inclination angle $\theta_t'$ with the boundary line BL that corresponds to a vertical surface of the panel 200c.

The two lenses 130 may include the first lens 130-1 and a second lens 130-2'. Unlike FIG. 9 or 11, the second lens 130-2' may be disposed in the same direction as the first lens 130-1. An image of the first curved area A2-1 may be reflected by the first portion 120a-t1 and thus be incident on the first lens 130-1. As described above, an image of the second curved area A2-2 may be reflected by the second portion 120a-t2 and subsequently by the first portion 120a-t1 and thus be incident on the second lens 130-2'.

Figure 14:
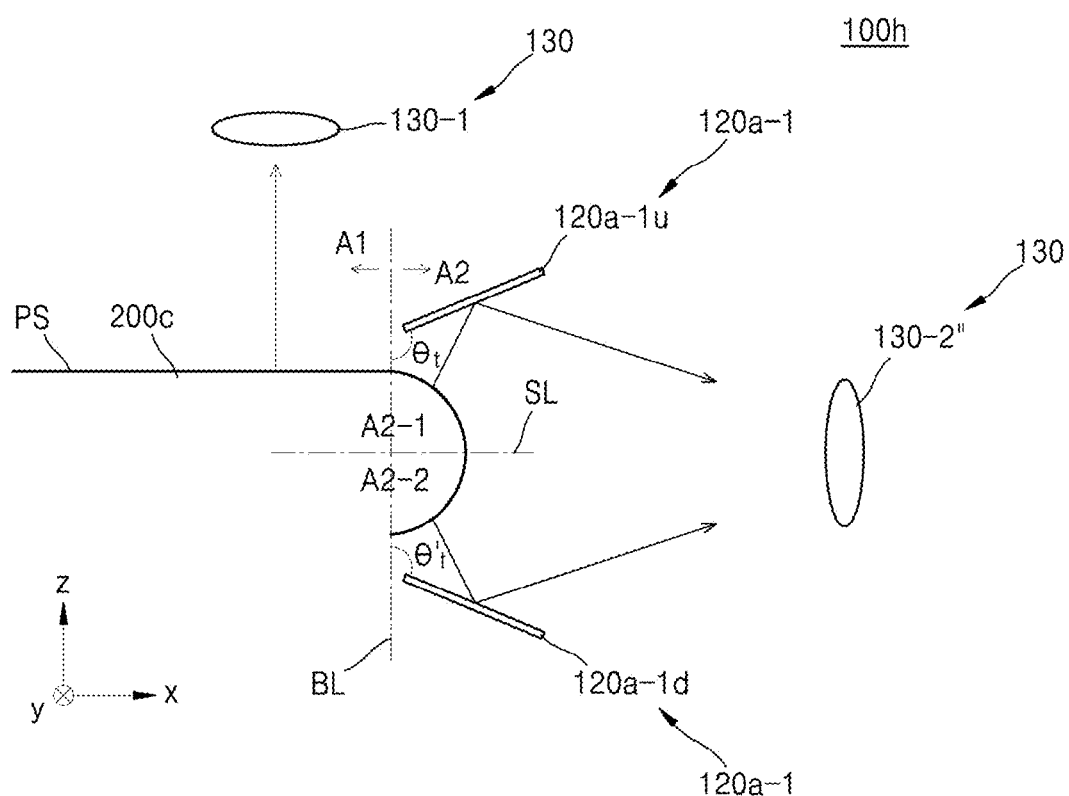

Referring to FIG. 14, the panel inspecting apparatus 100h according to the present example embodiment may be similar to the panel inspecting apparatus 100e of FIG. 11 in that two first mirrors 120a-1 and two lenses 130 are included. However, respective inclination angles of the two first mirrors 120a-1 and a position of a second lens 130-2" of the panel inspecting apparatus 100h according to the present example embodiment may be different from those of the panel inspecting apparatus 100e of FIG. 11.

For example, the two first mirrors 120a-1 may include the first upper mirror 120a-1u and the first lower mirror 120a-1d. The first upper mirror 120a-1u may be disposed at a first inclination angle $\theta_t$ with respect to the boundary line BL that corresponds to the vertical surface of the panel 200c, and the first lower mirror 120a-1d may be disposed at a second inclination angle $\theta_t'$ with respect to the boundary line BL. When the first curved area A2-1 and the second curved area A2-2 are symmetric about the central line SL, the first inclination angle $\theta_t$ may be the same as the second inclination angle $\theta_t'$. However, even when the first curved area A2-1 and the second curved area A2-2 are symmetric about the central line SL, the first inclination angle $\theta_t$ may not be the same as the second inclination angle $\theta_t'$. Also, when the first curved area A2-1 and the second curved area A2-2 are not symmetric about the central line SL, the first inclination angle $\theta_t$ may not be the same as the second inclination angle $\theta_t'$, or in some example embodiments, the first inclination angle $\theta_t$ may be the same as the second inclination angle $\theta_t'$.

The two lenses 130 may include the first lens 130-1 and the second lens 130-2". The first lens 130-1 may be the same as the first lens 130-1 of FIG. 9 or 11. The second lens 130-2" may be disposed toward the curved area A2, unlike FIG. 9 or 11. For example, a normal line of the second lens 130-2" may be parallel to the central line SL. In this structure of the second lens 130-2", an image of the curved area A2 may be reflected by the first mirror 120a-1, proceed in the first direction (x direction), and thus be incident on the second lens 130-2". For example, an image of the first curved area A2-1 may be reflected by the first upper mirror 120a-1u and thus be incident on the second lens 130-2", and an image of the second curved area A2-2 may be reflected by the first lower mirror 120a-1d and thus be incident on the second lens 130-2". An image of the flat area A1 of the panel 200c may be directly incident on the first lens 130-1.

Figure 15:
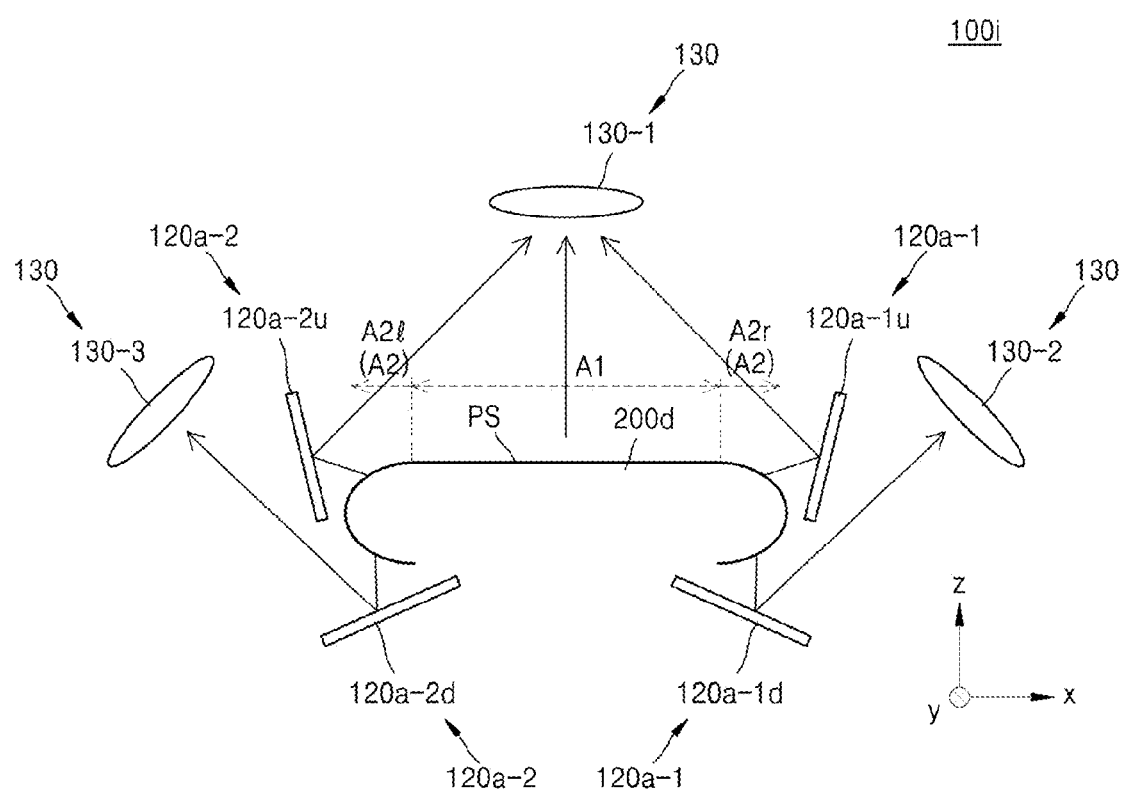
FIGS. 15 to 17 are conceptual views of panel inspecting apparatuses according to some example embodiments.
Figure 16:
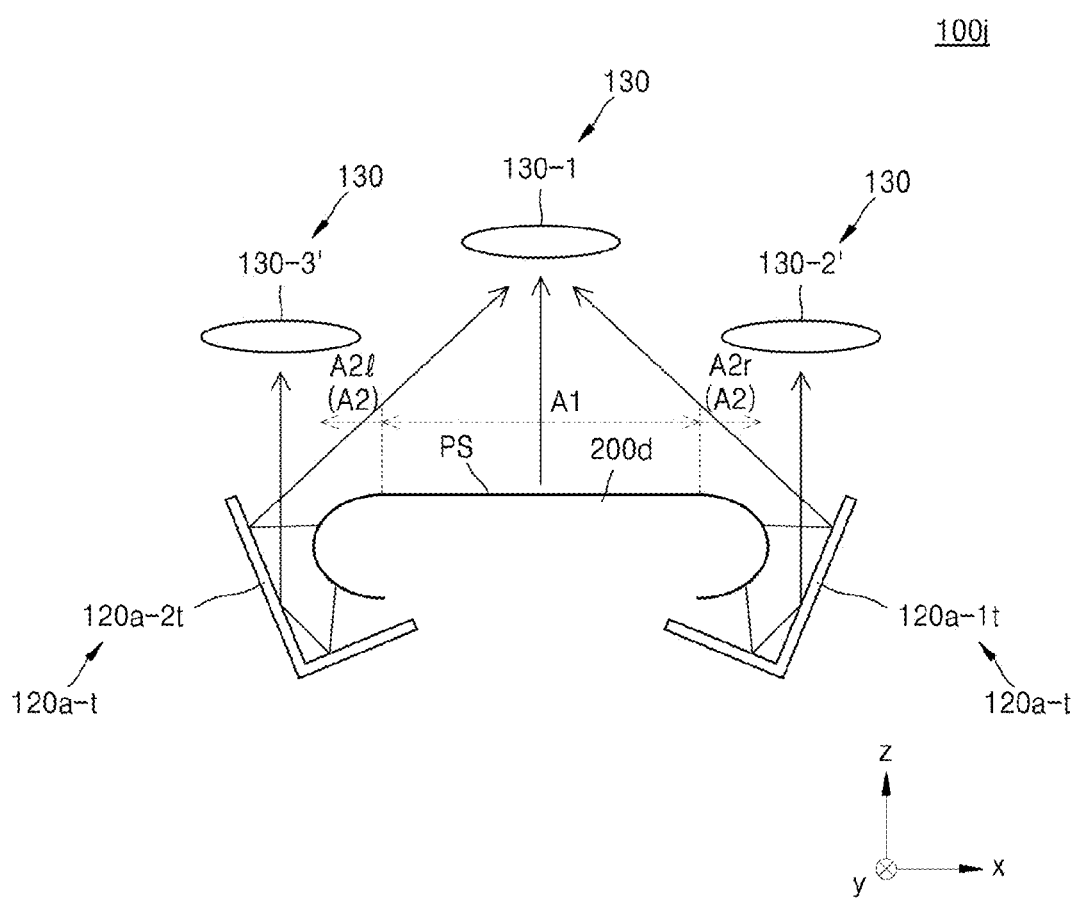
Figure 17:
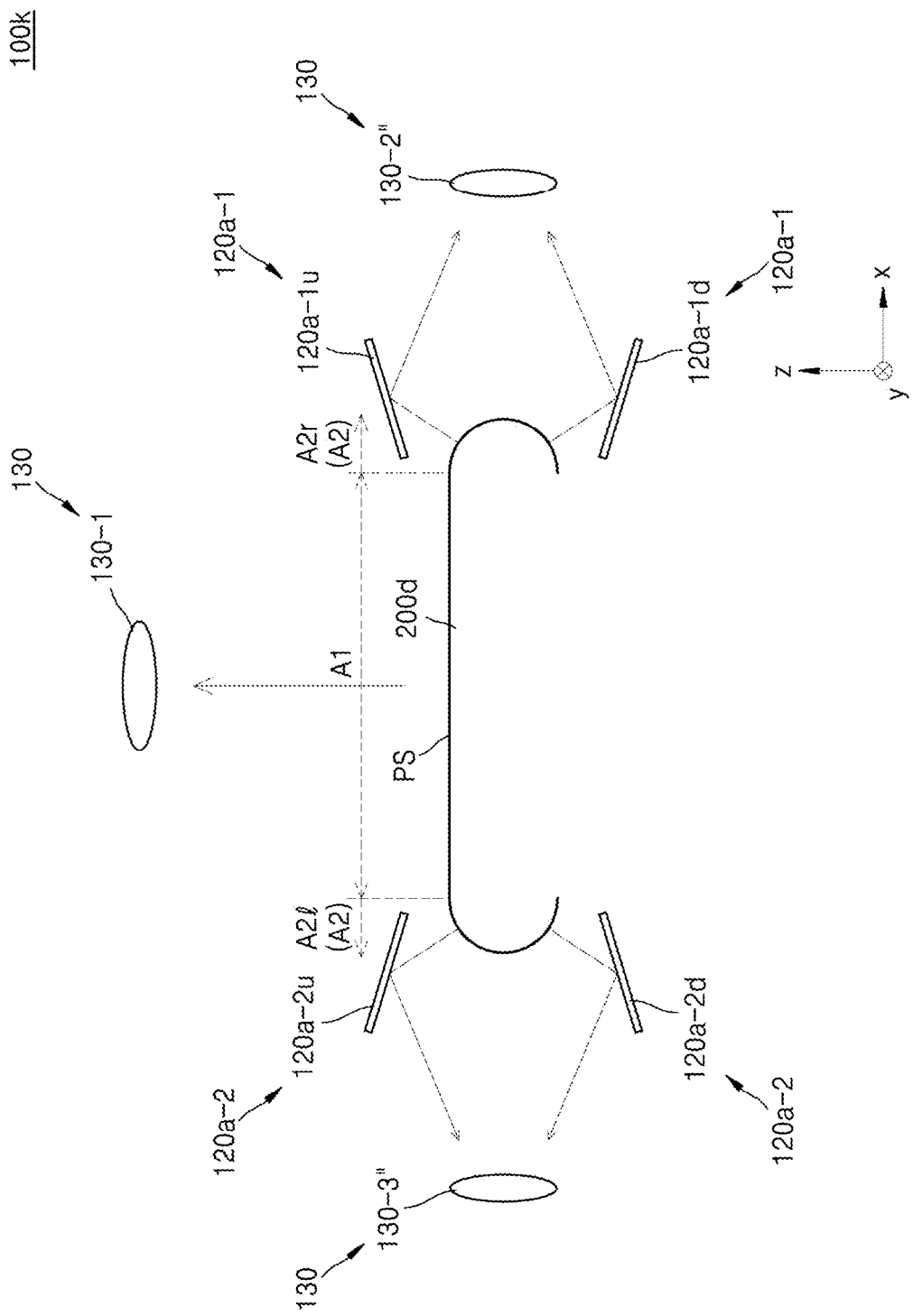

FIGS. 15 to 17 are conceptual views of panel inspecting apparatuses according to some example embodiments. For convenience of description, features and elements described with reference to FIGS. 11, 13, and 14 will be simply described or not be repeated.

Referring to FIG. 15, a panel inspecting apparatus 100i according to the present example embodiment may include four mirrors and three lenses 130. For example, the four mirrors may include two first mirrors 120a-1 at the right side of a panel 200d and two second mirrors 120a-2 at the left side of the panel 200d.

The panel 200d may include curved areas A2 along the second direction (y direction) at both edges thereof in the first direction (x direction). For example, the curved areas A2 may include a right curved area A2r disposed at the right edge of the panel 200d and a left curved area A2l disposed at the left edge of the panel 200d. A flat area A1 may be disposed between the right curved area A2r and the left curved area A2l. The right curved area A2r and the left curved area A2l may have the same or different shapes.

The right curved area A2r and the left curved area A2l may each include a first curved area and a second curved area, as shown in FIG. 9. Therefore, in the panel inspecting apparatus 100i according to the present example embodiment, two mirrors may be disposed with respect to each of the curved areas A2. For example, the two first mirrors 120a-1 may be disposed with respect to the right curved area A2r, and the two second mirror 120a-2 may be disposed with respect to the left curved area A2l. For example, a first upper mirror 120a-1u may be disposed corresponding to the first curved area of the right curved area A2r, and a first lower mirror 120a-1d may be disposed corresponding to the second curved area of the right curved area A2r. Similarly, a second upper mirror 120a-2u may be disposed corresponding to the first curved area of the left curved area A2l, and a second lower mirror 120a-2d may be disposed corresponding to the second curved area of the left curved area A2l.

The three lenses 130 may include a first lens 130-1, a second lens 130-2, and a third lens 130-3. An image of a flat area A1 may be directly incident on the first lens 130-1. Also, an image of the first curved area of the right curved area A2r may be reflected to the first lens 130-1 by the first upper mirror 120a-1u, and an image of the first curved area of the left curved area A2l may be reflected to the first lens 130-1 by the second upper mirror 120a-2u. An image of the second curved area of the right curved area A2r may be reflected to the second lens 130-2 by the first lower mirror 120a-1d, and an image of the second curved area of the left curved area A2l may be reflected to the third lens 130-3 by the second lower mirror 120a-2d.

Respective inclination angles of the two first mirrors 120a-1, respective inclination angles of the two second mirrors 120a-2, and respective positions of the second lens 130-2 and the third lens 130-3 are the same as described with reference to FIG. 9 or 11. Four mirrors of the panel inspecting apparatus 100i may be disposed perpendicularly or in parallel to the panel 200d, as shown in FIG. 9.

Referring to FIG. 16, a panel inspecting apparatus 100j according to the present example embodiment may include two combination mirrors 120a-t and three lenses 130. For example, the two combination mirrors 120a-t may include a first combination mirror 120a-1t disposed at the right side of the panel 200d and a second combination mirror 120a-2t disposed at the left side of the panel 200d.

The panel 200d may include curved areas A2 along the second direction at both edges thereof in the first direction, as described with reference to FIG. 15. For example, the curved areas A2 may include a right curved area A2r disposed at the right edge of the panel 200d and a left curved area A2l disposed at the left edge of the panel 200d. Also, the right curved area A2r and the left curved area A2l may each include a first curved area and a second curved area, as shown in FIG. 9. As described with reference to FIG. 13, a single combination mirror 120a-t may cover a first curved area and a second curved area that are included in a single curved area A2. Therefore, in the panel inspecting apparatus 100j according to the present example embodiment, one combination mirror 120a-t may be disposed with respect to each of the curved areas A2. For example, the first combination mirror 120a-1t may be disposed with respect to the right curved area A2r, and the second combination mirror 120a-2t may be disposed with respect to the left curved area A2l.

The three lenses 130 may include a first lens 130-1, a second lens 130-2', and a third lens 130-3'. As shown in FIG. 16, the second lens 130-2' and the third lens 130-3' may be disposed in the same direction as the first lens 130-1.

Respective coupling angles or inclination angles of a first portion and a second portion of the two combination mirrors 120a-t are the same as described with reference to FIG. 13. Also, descriptions regarding respective images of the right curved area A2r and the left curved area A2l being reflected by the combination mirror 120a-t and thus being respectively incident on the lenses 130-2' and 130-3' are the same as described with reference to FIG. 13.

Referring to FIG. 17, a panel inspecting apparatus 100k according to the present example embodiment may be similar to the panel inspecting apparatus 100i of FIG. 15. However, inclination angles of mirrors and positions of lenses may be different from the panel inspecting apparatus 100i of FIG. 15.

For example, the panel 200d may include a right curved area A2r disposed at a right side and a left curved area A2l disposed at a left side thereof. The panel inspecting apparatus 100k may include two first mirrors 120a-1 disposed at the right side of the panel 200d and two second mirrors 120a-2 disposed at the left side of the panel 200d. Also, the panel inspecting apparatus 100k may include a first lens 130-1, a second lens 130-2", and a third lens 130-3". The first lens 130-1 may be disposed toward a flat area A1, the second lens 130-2" may be disposed toward the right curved area A2r, and the third lens 130-3" may be disposed toward the left curved area A2l.

As described with reference to FIG. 14, the two first mirrors 120a-1 and the two second mirrors 120a-2 may be disposed at inclination angles $\theta_t$ and $\theta_t'$ with respect to a boundary line (BL of FIG. 14), and an image of the right curved area A2r may be reflected by the two first mirrors 120a-1 and thus be incident on the second lens 130-2", and an image of the left curved area A2l may be reflected by the two second mirrors 120a-2 and thus be incident on the third lens 130-3".

Figure 18:
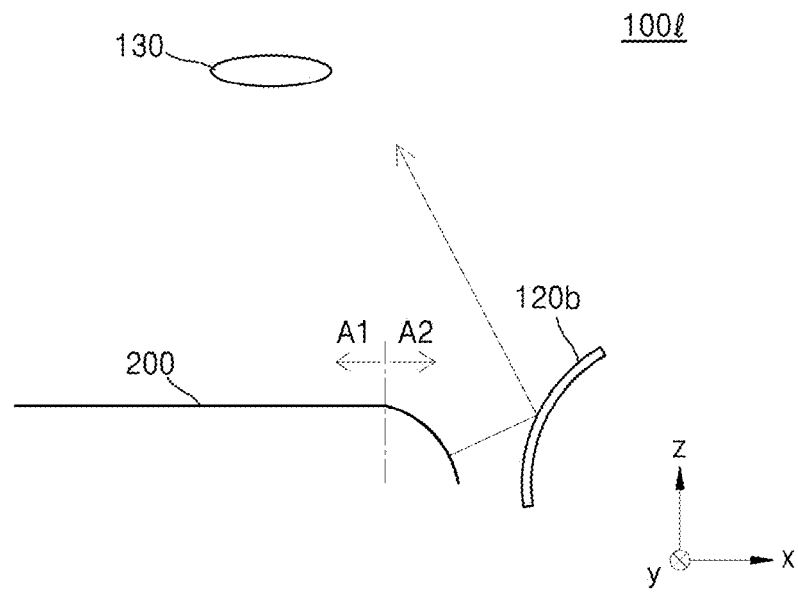
FIG. 18 is a conceptual view of a panel inspecting apparatus according to an example embodiment.

FIG. 18 is a conceptual view of a panel inspecting apparatus 100l according to an example embodiment.

Referring to FIG. 18, the panel inspecting apparatus 100l according to the present example embodiment may be similar to the panel inspecting apparatus 100 of FIG. 1 except that a curved mirror 120b is used instead of a flat mirror. In the panel inspecting apparatus 100l according to the present example embodiment, the curved mirror 120b may be, for example, a convex mirror that has a convex shape toward a curved area A2. A curvature of the curved mirror 120b may be the same as or different from a curvature of the curved area A2.

When the curvature of the curved mirror 120b is the same as the curvature of the curved area A2, a curved pattern of the curved area A2 may be changed to a flat mirror image, that is, a flat virtual image by the curved mirror 120b. Therefore, the pattern may be prevented from being distorted in any one direction of the pattern, for example, the first direction (x direction). However, because a virtual image becomes smaller than a real image due to characteristics of a convex mirror, the whole size of a pattern obtained via an image sensor (140 of FIG. 1) may be smaller than an actual size. Conversion of the pattern will be described with reference to FIG. 19.

Although in the panel inspecting apparatus 100l according to the present example embodiment, the panel 200 includes only one curved area A2, the present example embodiment is not limited thereto. For example, when the curved areas A2 are provided at both edges of the panel 200a, as shown in FIG. 6, two curved mirrors 120b may be disposed corresponding to each of the curved areas A2. Also, when the curved areas A2 are provided as in the panel 200c of FIG. 9 or the panel 200d of FIG. 15, the curved mirrors 120b may be disposed at corresponding curved areas, similarly to the flat mirrors.

Figure 19:
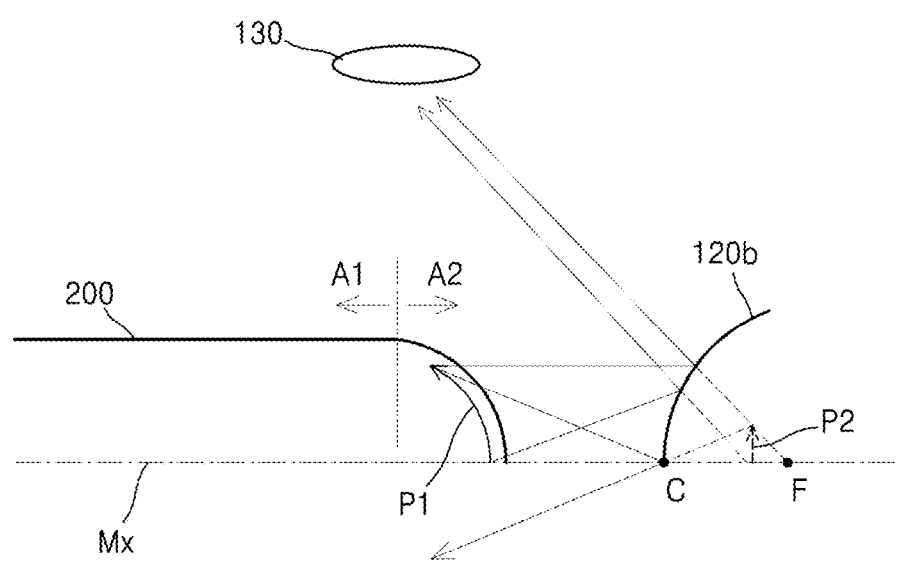
FIG. 19 is a conceptual view for describing a principle of forming a virtual image on a convex mirror in the panel inspecting apparatus of FIG. 18.

FIG. 19 is a conceptual view for describing a principle of forming a virtual image on a convex mirror in the panel inspecting apparatus 100l of FIG. 18.

Referring to FIG. 19, with respect to the curved mirror 120b that is a convex mirror, light follows the law of reflection: i) A light ray that is incident in parallel to a mirror axis Mx is reflected and then proceeds as if the light ray is emitted from a focus F. ii) The light ray that proceeds toward the focus F is reflected and then proceeds in parallel to the mirror axis Mx. iii) Light that is emitted toward a spherical center (exists on the mirror axis Mx) is reflected and returns back. iv) A light ray incident on a center C of the curved mirror 120b is reflected and then proceeds in directions that are symmetric about the mirror axis Mx.

Due to the law of reflection of the convex mirror as described above, a pattern P1 of a curve of the curved area A2 may be converted to a straight mirror image, that is, a pattern P2 of a straight virtual image, and then, the pattern P2 of the straight virtual image may be incident on the lens 130. However, as shown in FIG. 19, a size of the pattern P2 of the virtual image may be smaller than the pattern P1 of a real image. Therefore, a pattern obtained in an image sensor may be smaller than that of the pattern P1 of the real image.

Figure 20:
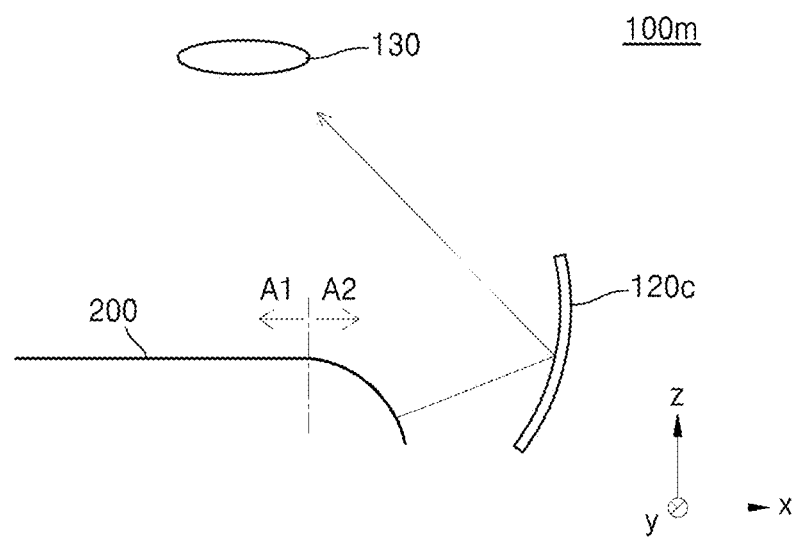
FIG. 20 is a conceptual view of a panel inspecting apparatus according to an example embodiment.

FIG. 20 is a conceptual view of a panel inspecting apparatus 100m according to an example embodiment.

Referring to FIG. 20, the panel inspecting apparatus 100m according to the present example embodiment may be similar to the panel inspecting apparatus 100 of FIG. 1 except that a curved mirror 120c is included instead of a flat mirror. In the panel inspecting apparatus 100m according to the present example embodiment, the curved mirror 120c may be, for example, a concave mirror that has a concave shape toward a curved area A2. A curvature of the curved mirror 120c may be the same as or different from a curvature of the curved area A2.

In the curved mirror 120c that is a concave mirror, a curved pattern of the curved area A2 may be converted to a more curved virtual image by the curved mirror 120c. Due to characteristics of the concave mirror, when a real image exists within a focus range of the concave mirror, an upright virtual image appears. The upright virtual image is larger than the real image. Therefore, the concave mirror may be used when a pattern of a curved area has to be enlarged. Conversion of the pattern will be described in detail with reference to FIG. 21.

Although in the panel inspecting apparatus 100m according to the present example embodiment, the panel 200 includes only one curved area A2, the present example embodiment is not limited thereto. For example, when the curved areas A2 are provided at both edges of the panel 200a, as shown in FIG. 6, two curved mirrors 120c may be disposed corresponding to each of the curved areas A2. Also, when the curved areas A2 are provided as in the panel 200c of FIG. 9 or the panel 200d of FIG. 15, the curved mirrors 120c may be disposed at corresponding curved areas, similarly to the flat mirrors. However, due to the characteristics of a concave mirror, a position of the concave mirror may be adjusted based on an angle at which an image is incident on the lens 130.

Figure 21:
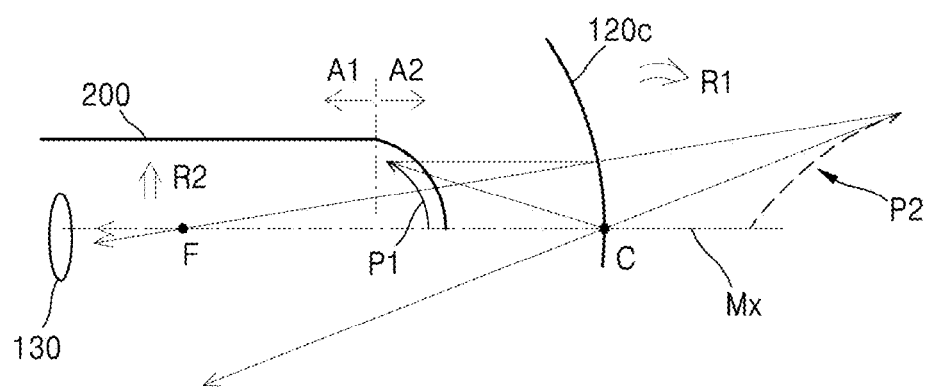
FIG. 21 is a conceptual view for describing a principle of forming a virtual image on a concave mirror in the panel inspecting apparatus of FIG. 20.

FIG. 21 is a conceptual view for describing a principle of forming a virtual image on the concave mirror 120c in the panel inspecting apparatus 100m of FIG. 20.

Referring to FIG. 21, with respect to the curved mirror 120c that is a concave mirror, light follows the law of reflection: i) A light ray that is incident in parallel to a mirror axis Mx is reflected, and then passes by a focus F. The light ray that passed by the focus F is reflected and then proceeds in parallel to the mirror axis Mx. iii) Light that passed by the spherical center (exists on the mirror axis Mx) is reflected and returns back. iv) A light ray incident on a center C of the curved mirror 120c is reflected and then proceeds in directions that are symmetric about the mirror axis Mx.

Due to the law of reflection of the concave mirror as described above, a curved pattern P1 of the curved area A2 may be converted to a more curved pattern P2 of a virtual image, and then, the more curved pattern P2 of the virtual image may be incident on the lens 130. However, as shown in FIG. 21, when the curved mirror 120c is disposed having the same mirror axis Mx as the curved area A2, an image reflected by the curved mirror 120c proceeds toward the focus F that is located inside the panel 200, and thus, it is difficult to set a position of the lens 130. Therefore, the curved mirror 120c may be rotated in a clockwise direction like a first thick arrow R1, and thus move the focus F above the panel 200 as indicated with a second thick arrow R2. By locating the lens 130 at an area to which the focus F is moved, an image reflected by the curved mirror 120c may be captured. A size of the pattern P2 of the virtual image may be larger than a pattern P1 of a real image. When the pattern P1 of the real image is located outside the focus F, an inverted real image may appear.

Figure 22:
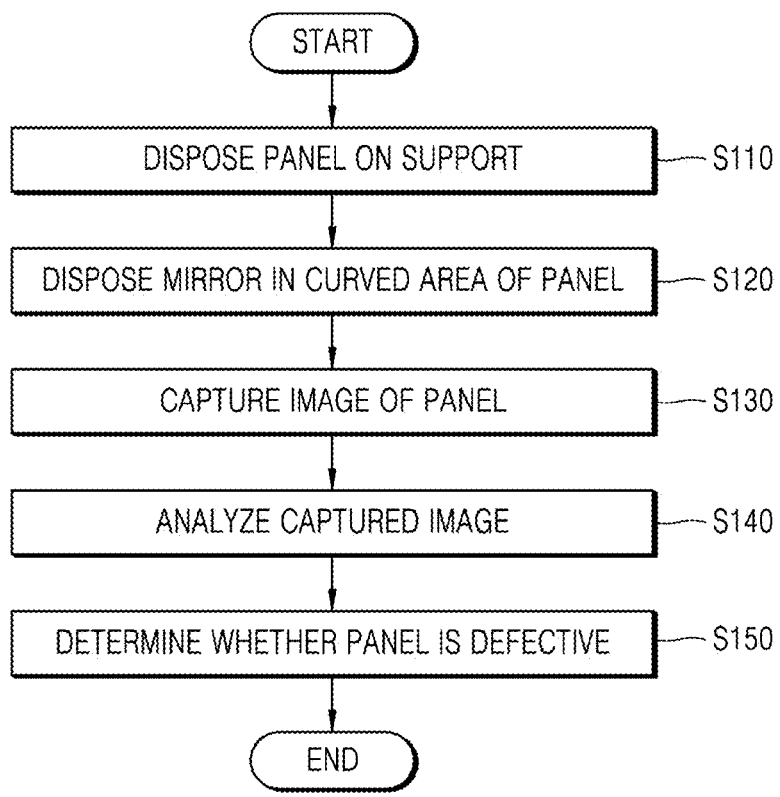
FIG. 22 is a flowchart of a method of inspecting a panel, according to an example embodiment.

FIG. 22 is a flowchart of a method of inspecting a panel, according to an example embodiment. For convenience of description, the method is described with reference to FIGS. 1 and 2.

Referring to FIG. 22, first, the method of inspecting the panel according to the present example embodiment includes disposing the panel 200 on the support 110 (S110). The panel 200 may include the flat area A1 and the curved area A2. As described with reference to FIGS. 8A to 8C, the curved area A2 may be disposed on at least one end of the flat area A1. The panel 200 may be disposed on the support 110 by using the substrate 250 as a medium. According to some example embodiments, the panel 200 may be disposed on the support 110 without the substrate 250 therebetween. When the substrate 250 is not included, a component, which has an upper surface that corresponds to a shape of a lower surface of the panel 200, may be formed on the support 110, and the panel 200 may be supported by the component.

Second, a mirror (120 or 120a) may be disposed on the curved area A2 of the panel 200. The mirror (120 or 120a) may be disposed perpendicular to the panel 200, as shown in FIG. 1A, or disposed at the first inclination angle $\theta_t$, as shown in FIG. 2. A position or an inclination angle of the mirror (120 or 120a) may be adjusted to obtain an optimal image of the curved area A2. For example, when the mirror 120 is disposed perpendicularly, a distance between the curved area A2 to the mirror 120 may be adjusted to ensure a viewing angle. Alternatively, when the mirror 120a is inclined, the first inclination angle $\theta_t$ and a distance between the curved area A2 and the mirror 120a may be adjusted based on a viewing angle, brightness of an image, and reducing pattern distortion.

Third, an image of the panel 200 may be captured (S130). For example, the panel 200 is driven, pixels of the panel 200 are turned on into a desired (or alternatively, predetermined) pattern, and light having the desired (or alternatively, predetermined) pattern is emitted to the outside. Emitted light may be directly incident on the lens 130 or reflected to the lens 130 by the mirror (120 or 120a). The lens 130 may focus the incident light and transmit the focused light to the image sensor 140. The image sensor 140 may capture light focused by the lens 130, and thus capture an image of the desired (or alternatively, predetermined) pattern. As shown in FIG. 1A, 1B, or 2, images of the flat area A1 may be directly captured, and images of the curved area A2 may be captured by being reflected by the mirror (120 or 120a).

After the images are captured, the analyzing unit 150 may analyze data of the captured images (S140). For example, the image sensor 140 may store the captured images as image data or image files, which are digital signals. The image data may be transferred to the analyzing unit 150, and the analyzing unit 150 may analyze the received image data.

Then, based on an analysis result of the image data, the analyzing unit 150 may determine whether the panel 200 is defective (S150). The determining may be performed by using an existing optical system for inspecting image quality of a flat display panel. When a mirror is used as in the method of inspecting the panel, according to the present example embodiment, since the curved area A2 is darker than the flat area A1, a defect determining standard of the curved area A2 may be relatively less strict than that of the flat area A1. A defect of a panel may include faulty pixels, distortion of a pattern (that is, a group of pixels), or brightness specks (mura).

The analysis result of the image data analyzed by the analyzing unit 150 may be provided as feedback data for a manufacturing process of the panel 200 before inspecting image quality. The feedback data may be used to find and solve a cause of the defect in the panel 200.

Figure 23:
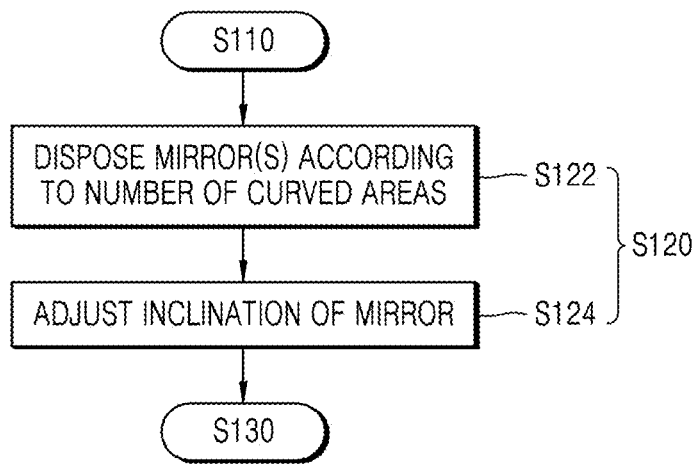
FIG. 23 is a flowchart of a detailed example of disposing a mirror in a curved area (operation S120), in the method of inspecting the panel of FIG. 22, according to an example embodiment.

FIG. 23 is a flowchart of a detailed example of disposing a mirror in the curved area A2 (operation S120), in the method of inspecting the panel 200 of FIG. 22, according to an example embodiment.

Referring to FIG. 23, after the panel 200 may be disposed on the support 110 (S110), the mirror may be disposed (S120). The disposing of the mirror (S120) may include the two following operations: First, a plurality of mirrors may be disposed according to the number of curved areas A2 (S122). For example, when there is only one curved area A2, as shown in FIGS. 1A, 1B, and 2, one mirror (120 or 120a) may be disposed. Also, when there are a plurality of curved areas A2, as shown in FIGS. 8B and 8C, a plurality of mirrors (120 or 120a) may be disposed.

When the curved area A2 of the panel 200 includes the first curved area A2-1 and the second curved area A2-2, as shown in FIGS. 10A to 10C, two mirrors (120 or 120a) may be disposed per each curved area A2, or one combination mirror 120a-t may be disposed as shown in FIG. 13.

After an appropriate number of mirrors are disposed, an inclination of each mirror may be adjusted (S124). For example, an inclination angle of the mirror 120a may be adjusted based on a radius of curvature of the curved area A2, an incident angle of the mirror 120a, and an incident angle with respect to the lens 130. When the mirrors are perpendicular or parallel to a panel (200 or 200c), as shown in FIG. 1A or 9, the adjusting of the inclination (S124) may be omitted. After the adjusting of the inclination (S124), the method proceeds to the capturing of the image (S140).

As described above, according to the one or more of the above example embodiments, apparatuses and/or methods of inspecting a panel may solve the non-uniform brightness problem and the pattern distortion problem of a curved area by capturing an image of the curved area by using a mirror disposed near the curved area of a panel. Accordingly, it may be accurately inspected whether image quality of the curved area of the panel is defective. Further, because a structure is simplified, inspecting of an image quality defect of a panel may be conveniently performed with small cost and in a short time.

Also, even when a curved area of a panel (that is an object to be inspected) is shaped as a circular arc having a central angle of 90° or more, the apparatuses and/or the methods according to the above example embodiments may conveniently and accurately inspect the image quality of the curved area of the panel by using two or more mirrors.

While the inventive concepts have been particularly shown and described with reference to example embodiments thereof, it will be understood that various changes in form and details may be made therein without departing from the spirit and scope of the following claims.

What is claimed is:

1. A panel inspecting apparatus comprising:
   a support on which a panel is disposed, the panel including a flat area, and at least one curved area, the flat area being parallel to an upper surface of the support, the at least one curved area extending from the flat area;
   at least one mirror corresponding to the at least one curved area of the panel, the at least one mirror being a flat mirror, the at least one mirror and the panel being horizontally arranged such that the at least one mirror faces an end of the panel and a surface of the at least one mirror is perpendicular to the flat area of the panel;
   at least one lens provided in parallel with the upper surface of the support, the at least one lens configured to receive an image from the panel and an image reflected by the at least one mirror without converting a propagation direction of the reflected image; and
   an image sensor configured to capture the images transferred via the at least one lens.

2. The panel inspecting apparatus of claim 1, wherein the at least one curved area is a plurality of curved areas,
   the at least one mirror is a plurality of mirrors, a number of the plurality of mirrors corresponds to a number of the plurality of curved areas, and
   at least one of the plurality of mirrors is near the at least one curved area.

3. The panel inspecting apparatus of claim 2, wherein the panel extends in a direction,
   the plurality of curved areas include one curved area at one edge of the panel and another curved areas at an opposite edge of the panel in the direction,
   the plurality of mirrors include two mirrors corresponding to the two curved areas, respectively, and
   the two mirrors face each other.

4. The panel inspecting apparatus of claim 1, wherein the at least one curved area includes a first curved area, a normal line of which forms an angle of 90° or less with respect to a normal line of the flat area, and a second curved area, a normal line of which forms an obtuse angle with respect to the normal line of the flat area.

5. The panel inspecting apparatus of claim 4, wherein the at least one mirror includes a first mirror corresponding to the first curved area and a second mirror corresponding to the second curved area, and
   the at least one lens includes a first lens configured to receive an image of the first curved area via the first mirror and a second lens configured to receive an image of the second curved area via the second mirror.

6. The panel inspecting apparatus of claim 4, wherein the at least one mirror has a structure including a first portion and a second portion coupled to the first portion at an angle, a first portion corresponds to the first curved area, and a second portion corresponds to the second curved area are coupled at an angle, and
   the at least one lens includes a first lens configured to receive an image of the first curved area via the first portion and a second lens configured to receive an image of the second curved area one of directly from the second portion and from the first and second portions.

7. The panel inspecting apparatus of claim 4, wherein the panel extends in a direction,
   the at least one curved area includes first two curved areas at a first edge of the panel and second two curved areas at a second edge of the panel, the first and second edges being opposite in the direction, the first two curved areas including a first upper curved area and a first lower curved area, the second two curved areas including a second upper curved area and a second lower curved area,
   the at least one mirror includes first two mirrors corresponding to the first two curved areas and second two mirrors corresponding to the second two curved areas, and
   the at least one lens includes a first lens configured to receive images of the first upper curved area and the second upper curved area, a second lens configured to receive an image of any one of the first lower curved area and the second lower curved area, and a third lens configured to receive an image of the other one of the first lower curved area and the second lower curved area.

8. The panel inspecting apparatus of claim 4, wherein the panel extends in a direction,
   the at least one curved area includes two sets of the first and second curved areas at two opposite edges of the panel in the direction, respectively,
   the at least one mirror is two mirrors, each of which corresponds to one of the two sets of the first and second curved areas at a corresponding one of the both edges,
   the two mirrors each have a structure including a first portion and a second portion coupled to the first portion at an angle, the first portion corresponds to the first curved area, and a second portion corresponds to the second curved area, and
   the at least one lens includes a first lens configured to receive images of the two first curved area at the two opposite edges, a second lens configured to receive an image of any one of the two second curved areas at the two opposite edges, and a third lens configured to receive an image of the other one of the two second curved areas at the two opposite edges.

9. The panel inspecting apparatus of claim 1, wherein the mirror is a curved mirror.

10. The panel inspecting apparatus of claim 9, wherein the panel includes a flat area and a curved area, the flat area is parallel to an upper surface of the support, and a curved area extends from the flat area and is curved toward the support,
    the at least one mirror is a plurality of mirrors and the at least one curved area is a plurality of curved areas, a number of the plurality of mirrors corresponds to a number of the plurality of curved areas, and the at least one mirrors each is near a corresponding one of the at least one curved area, and the at least one mirrors is a convex mirror that has a convex shape toward the curved area.

11. The panel inspecting apparatus of claim 10, wherein the mirror has a radius of curvature at which a virtual image of a pattern of the at least one curved area is flattened.

12. A panel inspecting apparatus comprising:
a support configured to receive a panel on an upper surface thereof, the panel including a flat area and a curved area, the curved area defined at an end of the panel;
at least one mirror configured to reflect an image of the curved area of the panel, the at least one mirror being a flat mirror, the at least one mirror and the panel being horizontally arranged such that the at least one mirror faces the end of the panel and a surface of the at least one mirror is perpendicular to or inclined at an angle with respect to the flat area of the panel;
at least one lens provided in parallel with the upper surface of the support, the at least one lens configured to receive image information of the flat area and image information of the curved area reflected from the at least one mirror without converting a propagation direction of the reflected image information of the flat area and the reflected image information of the curved area; and
an image sensor configured to convert the image information of the flat area and the image information of the curved area received via the lens to electric signals.

13. The panel inspecting apparatus of claim 12, wherein the at least one mirror is a plurality of mirrors, and the plurality of mirrors are configured to correspond to a plurality of radii of curvatures of the curved area.

14. The panel inspecting apparatus of claim 12, wherein the at least one mirror is a plurality of mirrors and some of the plurality of mirrors correspond to a single lens of the at least one lens.

15. The panel inspecting apparatus of claim 12, wherein the at least one mirror is a plurality of mirrors, the at least one lens is a plurality of lens, and the plurality of mirrors are configured to correspond to the plurality of lens.

* * * * *